United States Patent
Harrison et al.

(10) Patent No.: US 8,034,628 B2
(45) Date of Patent: *Oct. 11, 2011

(54) APPARATUS AND METHOD FOR TRAPPING BEAD BASED REAGENTS WITHIN MICROFLUIDIC ANALYSIS SYSTEMS

(75) Inventors: D. Jed Harrison, Edmonton (CA); Richard Oleschuk, Kingston (CA); Loranelle Shultz-Lockyear, Durango, CO (US); Cameron Skinner, Montreal (CA); Paul Li, Burnaby (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.
This patent is subject to a terminal disclaimer.

(21) Appl. No.: 12/831,949

(22) Filed: Jul. 7, 2010

(65) Prior Publication Data
US 2010/0326826 A1    Dec. 30, 2010

Related U.S. Application Data

(63) Continuation of application No. 11/955,902, filed on Dec. 13, 2007, now abandoned, which is a continuation of application No. 10/148,425, filed on Nov. 4, 2002, now Pat. No. 7,312,611.

(51) Int. Cl.
*G01N 1/18* (2006.01)
*G01N 31/20* (2006.01)

(52) U.S. Cl. ............ 436/177; 73/863.23; 422/503; 422/504; 422/507; 422/527; 435/287.3; 435/288.5; 436/178; 436/180

(58) Field of Classification Search ........... 210/198.2, 210/263, 348, 435, 459, 511; 204/450, 451, 204/600, 601; 422/68.1, 69, 70, 100, 101, 422/502, 504, 507, 503, 527; 435/6, 7.1, 435/7.2, 287.1, 287.2, 287.7, 288.2, 288.3, 435/288.4, 288.5, 287.3; 436/177, 178, 180; 73/863.23

See application file for complete search history.

(56) References Cited

U.S. PATENT DOCUMENTS 3,352,643 A    11/1967 Ando et al.
(Continued)

FOREIGN PATENT DOCUMENTS

EP    0459241 B1    12/1991
(Continued)

OTHER PUBLICATIONS

Datasheet Cycle Sequencing, Retrieved from the internet, URL:http//answers.com/topic/cycle sequencing. Printed Sep. 3, 2010, pp. 1-2.
European search report dated Sep. 1, 2010 for Application No. 5804847.1.
International search report dated Oct. 6, 2010 for PCT Application No. US10/37545.
International search report dated Aug. 18, 2009 for PCT Application No. US09/00419.
(Continued)

*Primary Examiner* — Joseph Drodge
(74) *Attorney, Agent, or Firm* — Wilson Sonsini Goodrich & Rosati

(57) ABSTRACT

An on-chip packed reactor bed design is disclosed that allows for an effective exchange of packing materials such as beads at a miniaturized level. Also disclosed is a method of treating a sample within a microfluidic analysis system, comprising; providing a main channel having a trapping zone; providing a slurry of a reagent treated packing material; inducing a flow of said packing material into said trapping zone through a flow channel connected to said trapping zone to load said trapping zone and form a packed bed of said packing material; and flowing a sample containing analytes through said packed bed, said reagent treating the sample. The present invention extends the function of microfluidic analysis systems to new applications including on-chip solid phase extraction (SPE) and on-chip capillary electrochromatography (CEC). The design can be further extended to include integrated packed bed immuno- or enzyme reactors.

10 Claims, 14 Drawing Sheets

U.S. PATENT DOCUMENTS

| | | |
|---|---|---|
| 3,433,257 A | 3/1969 | Jensen |
| 3,568,692 A | 3/1971 | Metzger et al. |
| 4,963,498 A | 10/1990 | Hillman et al. |
| 5,376,252 A | 12/1994 | Ekström et al. |
| 5,453,163 A | 9/1995 | Yan |
| 5,571,410 A | 11/1996 | Swedberg et al. |
| 5,587,128 A | 12/1996 | Wilding et al. |
| 5,635,358 A * | 6/1997 | Wilding et al. ............... 435/7.2 |
| 5,639,428 A * | 6/1997 | Cottingham ................ 422/112 |
| 5,705,813 A | 1/1998 | Apffel et al. |
| 5,726,026 A | 3/1998 | Wilding et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |
| 5,776,748 A * | 7/1998 | Singhvi et al. ............... 435/180 |
| 5,842,787 A | 12/1998 | Kopf-sill et al. |
| 5,856,174 A | 1/1999 | Lipshutz et al. |
| 5,863,502 A | 1/1999 | Southgate et al. |
| 5,872,010 A * | 2/1999 | Karger et al. ............... 436/173 |
| 5,885,470 A | 3/1999 | Parce et al. |
| 5,908,552 A | 6/1999 | Zimmerman et al. |
| 5,922,591 A | 7/1999 | Anderson et al. |
| 5,942,443 A | 8/1999 | Parce et al. |
| 5,948,684 A * | 9/1999 | Weigl et al. ................ 436/52 |
| 5,971,158 A | 10/1999 | Yager et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,120,184 A | 9/2000 | Laurence et al. |
| 6,136,212 A | 10/2000 | Mastrangelo et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor, Jr. et al. |
| 6,321,791 B1 | 11/2001 | Chow |
| 6,322,683 B1 | 11/2001 | Wolk et al. |
| 6,348,318 B1 | 2/2002 | Valkirs |
| 6,379,929 B1 | 4/2002 | Burns et al. |
| 6,387,707 B1 * | 5/2002 | Seul et al. .................. 436/164 |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,290 B1 | 8/2002 | Harrison et al. |
| 6,454,924 B2 | 9/2002 | Jedrzejewski et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,532,997 B1 | 3/2003 | Bedingham et al. |
| 6,533,914 B1 | 3/2003 | Liu |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein et al. |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,663,833 B1 | 12/2003 | Stave et al. |
| 6,685,442 B2 | 2/2004 | Chinn et al. |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,824,663 B1 | 11/2004 | Boone |
| 6,829,753 B2 | 12/2004 | Lee et al. |
| 6,852,287 B2 | 2/2005 | Ganesan |
| 6,870,185 B2 | 3/2005 | Roach et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,198,759 B2 | 4/2007 | Bryning et al. |
| 7,279,146 B2 | 10/2007 | Nassef et al. |
| 7,282,361 B2 | 10/2007 | Hodge |
| 7,312,611 B1 | 12/2007 | Harrison et al. |
| 7,323,305 B2 | 1/2008 | Leamon et al. |
| 7,438,856 B2 | 10/2008 | Jedrzejewski et al. |
| 7,445,926 B2 | 11/2008 | Mathies et al. |
| 7,488,603 B2 | 2/2009 | Gjerde et al. |
| 7,745,207 B2 | 6/2010 | Jovanovich et al. |
| 7,763,453 B2 | 7/2010 | Clemmens et al. |
| 2001/0041357 A1 | 11/2001 | Fouillet et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0119480 A1 | 8/2002 | Weir et al. |
| 2002/0119482 A1 | 8/2002 | Nelson et al. |
| 2002/0139084 A1 | 10/2002 | Tobolka |
| 2002/0160361 A1 | 10/2002 | Loehrlein et al. |
| 2003/0008308 A1 | 1/2003 | Enzelberger et al. |
| 2003/0021734 A1 | 1/2003 | Vann et al. |
| 2003/0029724 A1 | 2/2003 | Derand et al. |
| 2003/0070677 A1 | 4/2003 | Handique et al. |
| 2003/0217923 A1 | 11/2003 | Harrison et al. |
| 2004/0014091 A1 | 1/2004 | Duck et al. |
| 2004/0037739 A1 | 2/2004 | Mcneely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086870 A1 | 5/2004 | Tyvoll et al. |
| 2004/0086872 A1 | 5/2004 | Childers et al. |
| 2004/0132170 A1 | 7/2004 | Storek et al. |
| 2004/0151629 A1 | 8/2004 | Pease et al. |
| 2004/0197845 A1 | 10/2004 | Hassibi et al. |
| 2004/0209354 A1 | 10/2004 | Mathies et al. |
| 2004/0224380 A1 | 11/2004 | Chou et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0161326 A1 | 7/2005 | Morita et al. |
| 2005/0161669 A1 | 7/2005 | Jovanovich et al. |
| 2005/0224134 A1 | 10/2005 | Yin et al. |
| 2005/0224352 A1 | 10/2005 | Harrison et al. |
| 2005/0241941 A1 | 11/2005 | Parce et al. |
| 2005/0255003 A1 | 11/2005 | Summersgill et al. |
| 2005/0287572 A1 | 12/2005 | Mathies et al. |
| 2006/0027456 A1 | 2/2006 | Harrison et al. |
| 2006/0057209 A1 | 3/2006 | Chapman et al. |
| 2006/0073484 A1 | 4/2006 | Mathies et al. |
| 2006/0076068 A1 | 4/2006 | Young et al. |

| | | | |
|---|---|---|---|
| 2006/0140051 A1 | 6/2006 | Kim et al. | |
| 2006/0163143 A1 | 7/2006 | Chirica et al. | |
| 2006/0186043 A1 | 8/2006 | Covey et al. | |
| 2006/0266645 A1 | 11/2006 | Chen et al. | |
| 2007/0017812 A1 | 1/2007 | Bousse | |
| 2007/0034025 A1 | 2/2007 | Pant et al. | |
| 2007/0105163 A1 | 5/2007 | Grate et al. | |
| 2007/0122819 A1 | 5/2007 | Wu et al. | |
| 2007/0175756 A1 | 8/2007 | Nguyen et al. | |
| 2007/0184463 A1 | 8/2007 | Molho et al. | |
| 2007/0202531 A1 | 8/2007 | Grover | |
| 2007/0237686 A1 | 10/2007 | Mathies et al. | |
| 2007/0238109 A1 | 10/2007 | Min et al. | |
| 2007/0248958 A1 | 10/2007 | Jovanovich et al. | |
| 2007/0297947 A1 | 12/2007 | Sommers et al. | |
| 2008/0014576 A1 | 1/2008 | Jovanovich et al. | |
| 2008/0047836 A1 | 2/2008 | Strand et al. | |
| 2008/0124723 A1 | 5/2008 | Dale et al. | |
| 2008/0164155 A1 | 7/2008 | Pease et al. | |
| 2008/0179255 A1 | 7/2008 | Jung et al. | |
| 2008/0237146 A1 | 10/2008 | Harrison et al. | |
| 2008/0281090 A1 | 11/2008 | Lee et al. | |
| 2008/0302732 A1 | 12/2008 | Soh et al. | |
| 2008/0311585 A1 | 12/2008 | Gao et al. | |
| 2009/0004494 A1 | 1/2009 | Blenke et al. | |
| 2009/0035770 A1 | 2/2009 | Mathies et al. | |
| 2009/0053799 A1 | 2/2009 | Chang-yen et al. | |
| 2009/0056822 A1 | 3/2009 | Young et al. | |
| 2009/0060797 A1 | 3/2009 | Mathies et al. | |
| 2009/0084679 A1 | 4/2009 | Harrison et al. | |
| 2009/0134069 A1 | 5/2009 | Handique | |
| 2009/0137413 A1 | 5/2009 | Mehta et al. | |
| 2009/0148933 A1 | 6/2009 | Battrell et al. | |
| 2009/0181411 A1 | 7/2009 | Battrell et al. | |
| 2009/0253181 A1 | 10/2009 | Vangbo et al. | |
| 2009/0286327 A1 | 11/2009 | Cho et al. | |
| 2009/0311804 A1 | 12/2009 | Mcbrady et al. | |
| 2010/0068723 A1 | 3/2010 | Jovanovich et al. | |
| 2010/0165784 A1 | 7/2010 | Jovanovich et al. | |
| 2010/0303687 A1 | 12/2010 | Blaga et al. | |
| 2011/0005932 A1 | 1/2011 | Jovanovich et al. | |
| 2011/0027913 A1 | 2/2011 | Bau et al. | |

FOREIGN PATENT DOCUMENTS

| | | | |
|---|---|---|---|
| EP | 0637999 A1 | 2/1995 | |
| EP | 0527905 B1 | 11/1995 | |
| EP | 1065378 B1 | 4/2002 | |
| EP | 1411340 A2 | 4/2004 | |
| EP | 1411340 A3 | 5/2004 | |
| EP | 1658890 B1 | 5/2008 | |
| JP | 408327594 A | 12/1996 | |
| WO | WO 96/04547 A1 | 2/1996 | |
| WO | WO 98/52691 A1 | 11/1998 | |
| WO | WO 98/53300 A2 | 11/1998 | |
| WO | WO 98/53300 A3 | 2/1999 | |
| WO | WO 99/36766 A1 | 7/1999 | |
| WO | WO 99/40174 A1 | 8/1999 | |
| WO | WO 00/40712 A1 | 7/2000 | |
| WO | WO 00/60362 A1 | 10/2000 | |
| WO | WO 00/61198 | 10/2000 | |
| WO | WO 01/38865 A1 | 5/2001 | |
| WO | WO 01/85341 A1 | 11/2001 | |
| WO | WO 02/43615 A2 | 6/2002 | |
| WO | WO 02/043615 A3 | 3/2003 | |
| WO | WO 03/085379 | 10/2003 | |
| WO | WO 2004/098757 A2 | 11/2004 | |
| WO | WO 2005/075081 A1 | 8/2005 | |
| WO | WO 2004/098757 A3 | 5/2006 | |
| WO | WO 2009/129415 A1 | 10/2009 | |
| WO | WO 2010/041174 A1 | 4/2010 | |

OTHER PUBLICATIONS

International search report dated Sep. 25, 2007 for PCT Application No. US2007/02721.

International search report dated May 14, 2010 for PCT Application No. US2009/06640.

International search report dated Jul. 30, 2010 for PCT Application No. US2010/36464.

European search report dated Dec. 18, 2009 for Application No. 03808583.3.

International search report dated Apr. 5, 2001 for PCT Application No. CA2000/01421.

International search report dated Jul. 11, 2008 for PCT Application No. US07/61573.

International search report dated Aug. 23, 2006 for PCT Application No. US2005/033347.

International search report dated Aug. 26, 2004 PCT Application No. US2003/41466.

Jacobson, et al. Electrokinetic Focusing in Microfabricated Channel Structures. Anal. Chem., 1997, 69 (16), pp. 3212-3217.

Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. Accessed Jun. 2, 2010.

Wikipedia brochure for defining stocahstic process. Sep. 2, 2009.

Amendment and Request for Correction of Inventorship mailed Jan. 10, 2008 in U.S. Appl. No. 10/750,533.

Anderson, et al. A miniature integrated device for automated multistep genetic assays. Nucleic Acids Research. 2000;28:e60.

Blazej, et al. Microfabricated bioprocessor for integrated nanoliter-scale Sanger DNA sequencing. Proc. Natl. Acad. Sci. USA 2006;103:7240-7245.

Blazej, et al. Polymorphism Ratio Sequencing: A New Approach for Single Nucleotide Polymorphism Discovery and Genotyping. Genome Research. 2003;13:287-293.

Brenner, et al. Gene expression analysis by massively parallel signature sequencing (MPSS) on microbead arrays. Nature Biotechnology. 2000;18(6):630-634.

Buchholz, et al. The use of light scattering for precise characterization of polymers for DNA sequencing by capillary electrophoresis. Electrophoresis. 2001;22:4118-4128.

Coleman, et al. A sequential injection microfluidic mixing strategy. Microfluidics and Nanofluidics. 2005;319-327.

Curcio, et al. Continuous Segmented-Flow Polymerase Chain Reaction for High-Throughput Miniaturized DNA Amplification. Analytical Chemistry. 2003;75(1):1-7.

Diehl, et al. BEAMing: single-molecule PCR on microparticles in water-in-oil emulsions. Nature Methods. 2006;3(7):551-9.

Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.

Doherty, et al. Sparsely cross-linked "nanogels" for microchannel DNA sequencing. Electrophoresis. 2003;24(24):4170-4180.

Dorfman, et al. Contamination-Free Continuous Flow Microfluidic Polymerase Chain Reaction for Quantitative and Clinical Applications. Analytical Chemistry. 2005;77(11):3700-3704.

Doyle, et al. Self-Assembled Magnetic Matrices for DNA Separation Chips. Science. 2000;295:2237.

Dressman, et al. Transforming single DNA molecules into fluorescent magnetic particles for detection and enumeration of genetic variations. Proc Natl Acad Sci USA. 2003;100(15):8817-8822.

Emrich, et al. Microfabricated 384-Lane Capillary Array Electrophoresis Bioanalyzer for Ultrahigh-Throughput Genetic Analysis. Analytical Chemistry. 2002;74(19):5076-5083.

Ewing, et al. Base-Calling of Automated Sequencer Traces Using Phred. I. Accuracy Assessment. Genome Research. 1998;8:175-185.

Ewing, et al. Base-Calling of Automated Sequencer Traces Using Phred. II. Error probabilities. Genome Research. 1998;8:186-194.

Francis, et al. Flow analysis based on a pulsed flow of solution: theory, instrumentation and applications. Talanta. 2002;58(6):1029-1042.

Ghadessy, et al. Directed evolution of polymerase function by compartmentalized self-replication. Proc Natl Acad Sci USA. 2001;98:4552-4557.

Giddings, et al. A software system for data analysis in automated DNA sequencing. Genome Research. 1998;8:644-665.

Goll, et al. Microvalves with bistable buckled polymer diaphragms. Journal of Micromechanics and Microengineering. 1996;6:77-79.

Grover, et al. An integrated microfluidic processor for single nucleotide polymorphism-based DNA computing. Lab on a Chip. 2005;5(10):1033-1040.

Grover, et al. Development and multiplexed control of latching pneumatic valves using microfluidic logical structures. Lab on a chip. 2006;6:623-631.

Grover, et al. Monolithic membrane valves and diaphragm pumps for practical large-scale integration into glass microfluidic devices. Sensors and Actuators. 2003;B89:315-323.

Grover, et al. Practical Valves and Pumps for Large-Scale Integration into Microfludic Analysis Devices. Micro Total Analysis Systems. 2002;1:136-138.

Hansen, et al. A robust and scalable microfluidic metering method that allows protein crystal growth by free interface diffusion. Proc Natl Acad Sci USA. 2002;99(26):16531-16536.

Harrison, et al. Micromachining a Miniaturized Capillary Electrophoresis-Based Chemical Analysis System on a Chip. Science. 1993;261(5123):895-897.

Hayes, et al. EDGE: A Centralized Resource for the Comparison, Analysis, and Distribution of Toxicogenomic Information. Molecular Pharmacology. 2005;67(4):1360-1368.

Hultman, et al. Bidirectional Solid-Phase Sequencing of In Vitro-Amplified Plasmid DNA. BioTechniques. 1991;10(1):84-93.

International Preliminary Report for corresponding PCT Application No. PCT/CA2000/01421 dated Feb. 14, 2002.

International Preliminary Report for corresponding PCT Application No. PCT/US2005/018678 dated Nov. 13, 2007.

International Preliminary Report for corresponding PCT Application No. PCT/US2005/033347 dated Mar. 20, 2007.

International Preliminary Report for corresponding PCT Application No. PCT/US2007/007381 dated Sep. 23, 2008.

International Preliminary Report for corresponding PCT Application No. PCT/US2007/02721 dated Aug. 5, 2008.

International Preliminary Report for corresponding PCT Application No. PCT/US2007/061573 dated Aug. 26, 2008.

International Search Report for PCT/US2005/033347.

Ju, et al. Fluorescence energy transfer dye-labeled primers for DNA sequencing and analysis. Proc. Natl. Acad. Sci. USA. 1995;92:4347-4351.

Kan, et al. A novel thermogelling matrix for microchannel DNA sequencing based on poly-N-alkoxyalkylaclylamide copolymers. Electrophoresis. 2003;24(24):4161-4169.

Koh, et al. Integrating Polymerase Chain Reaction, Valving, and Electrophoresis in a Plastic Device for Bacterial Detection. Analytical Chemistry. 2003;75(17):4591-4598.

Lagally, et al. Fully integrated PCR-capillary electrophoresis microsystem for DNA analysis. Lab on a Chip. 2001;1(2):102-107.

Lagally, et al. Integrated Portable Genetic Analysis Microsystem for Pathogen/Infectious Disease Detection. Analytical Chemistry. 2004;76:3162-3170.

Lagally, et al. Monolithic integrated microfluidic DNA amplification and capillary electrophoresis analysis system. Sensors and Actuators. 2000;B63(3):138-146.

Lagally, et al. Single-Molecule DNA Amplification and Analysis in an Integrated Microfluidic Device. Analytical Chemistry. 2001;73(3): 565-570.

Lisec, et al. A bistable pneumatic microswitch for driving fluidic components. Sensors and Actuators. 1996;A54:746-749.

Liu, et al. Automated parallel DNA sequencing on multiple channel microchips. Proc. Natl. Acad. Sci. USA. 2000;97(10):5369-5374.

Liu, et al. Optimization of High-Speed DNA Sequencing on Microfabricated Capillary Electrophoresis Channels. Analytical Chemistry. 1999;71:566-573.

Margulies, et al. Genome sequencing in microfabricated high-density picolitre reactors. Nature. 2005;437(7057):376-80. (Abstact only).

Melin, et al. A Passive 2-Dimensional Liquid Sample Micromixer. 7th International Conference on Miniaturized Chemical and Biochemical Analysis Systems. 2003;167-170.

Mitra, et al. Digital genotyping and haplotyping with polymerase colonies. Proc Natl Acad Sci USA. 2003.100(10):15926-5931.

Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.

Office Action Final dated Feb. 19, 2008 issued in U.S. Appl. No. 10/540,658.

Office Action Final dated Feb. 6, 2008 issued in U.S. Appl. No. 11/139,018.

Office Action mailed Apr. 27, 2007 in U.S. Appl. No. 11/139,018, filed May 25, 2005.

Office Action mailed Jul. 2, 2007 in U.S. Appl. No. 10/540,658, filed Jun. 23, 2005.

Office Action mailed Jul. 12, 2007 in U.S. Appl. No. 10/750,533, filed Dec. 29, 2003.

Ohori, et al. Partly disposable three-way mirovalve for a medical micro total analysis system (muTAS). Sensors and Actuators. 1998;A64(1): 57-62.

Oleschuk, et al. Trapping of Bead-Based Reagents within Microfluidic Systems: On-Chip Solid-Phase Extraction and Electrochromatography. Analytical Chemistry. 2000;72:585-590.

Olsen, et al. Immobilization of DNA Hydrogel Plugs in Microfluidic Channels. Analytical Chemistry. 2002;74:1436-1441.

Paegel, et al. High-throughput DNA sequencing with a 96-lane capillary array electrophoresis bioprocessor. Proc Natl Acad Sci USA. 2002;99:574-579.

Paegel, et al. Microchip Bioprocessor for Integrated Nanovolume Sample Purification and DNA Sequencing. Analytical Chemistry. 2002;74(19):5092-5098.

Paegel, et al. Microfluidic devices for DNA sequencing: sample preparation and electrophoretic analysis. Current Opinion in Biotechnology. 2003;14(1):42-50.

Paegel, et al. Turn Geometry for Minimizing Band Broadening in Microfabricated Capillary Electrophoresis Channels. Analytical Chemistry. 2000;72:3030-3037.

PCT Notification of Transmittal of the International Search Report and the Written Opinion of the International Searching Authority, or the Declaration, mailed Jun. 17, 2008, Application No. PCT/US2007/082568.

Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.

Rohr, et al. Porous polymer monoliths: Simple and efficient mixers prepared by direct polymerization in the channels of microfluidic chips. Electrophoresis. 2001;22:3959-3967.

Rye, et al. High-sensitivity two-color detection of double-stranded DNA with a confocal fluorescence gel scanner using ethidium homodimer and thiazole orange. Nucleic Acids Research. 1991;19(2):327-333.

Scherer, et al. High-Pressure Gel Loader for Capillary Array Electrophoresis Microchannel Plates. Biotechniques. 2001;31(5):1150-1154.

Schomburg, et al. Design Optimization of Bistable Microdiaphragm Valves. Sensors and Actuators. 1998;A64:259-264.

Simpson, et al. High-throughput genetic analysis using microfabricated 96-sample capillary array electrophoresis microplates. Proc Natl Acad Sci USA. 1998;95:2256-2261.

Simpson, et al. Microfabrication Technology for the Production of Capillary Array Electrophoresis Chips. Biomedical Microdevices. 1998;1:7-26.

Soper, et al. Sanger DNA Sequencing Reactions Performed in a Solid-Phase Nanoreactor Directly Coupled to Capillary Gel Electrophoresis. Analytical Chemistry. 1998;70:4036-4043.

Takao, et al. A Pneumatically Actuated Full In-Channel Microvalve With MOSFET-Like Function in Fluid Channel Networks. Journal of Microelectromechanical Systems. 2002;11(5):421-426.

Takao, et al. Microfluidic Integrated Circuits for Signal Processing Using Analogous Relationship Betweeen Pneumatic Microvalve and MOSFET. Journal of Microelectromechanical Systems. 2003;12(4):497-505.

Thomas, et al. Application of Genomics to Toxicology Research. Environmental Health Perspectives. 2002;110(6):919-923.

Thorsen, et al. Microfluidic Large-Scale Integration. Science. 2002;298(5593):580-584.

Tice, et al. Formation of Droplets and Mixing in Multiphase Microfluidics at Low Values of the Reynolds and the Capillary Numbers. Langmuir. 2003;19:9127-9133.

Unger, et al. Monolithic Microfabricated Valves and Pumps by Multilayer Soft Lithography. Science. 2000;288:113-116.

Vazquez, et al. Electrophoretic Injection within Microdevices. Analytical Chemistry. 2002;74:1952-1961.

Veenstra, et al. The design of an in-plane compliance structure for microfluidical systems. Sensors and Actuators. 2002;B81:377-383.

Waller, et al. Quantitative Immunocapture PCR Assay for Detection of *Campylobacter jejuni* in Foods. Applied Environmental Microbiology. 2000; 66(9):4115-4118.

Weimer, et al. Solid-Phase Capture of Proteins, Spores, and Bacteria. Applied Environmental Microbiology. 2001;67(3):1300-1307.

Williams, et al. Amplification of complex gene libraries by emulsion PCR. Nature Methods. 2006;3(7):545-50.

Woolley, et al. Functional Integration of PCR Amplification and Capillary Electrophoresis in a Microfabricated DNA Analysis Device. Analytical Chemistry, 1996;68(23):4081-4086.

Yang, et al. A MEMS thermopneumatic silicone rubber membrane valve. Sensors and Actuators. 1998;A64(1):101-108.

Yu, et al. Preparation of Monolithic Polymers with Controlled Porous Properties for Microfluidic Chip Applications Using Photoinitiated Free Radial Polymerization. Journal of Polymer Science. 2002;40:755-769.

Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.

Bings, et al. Microfluidic Devices Connected to Fused-Silica Capillaries with Minimal Dead Dead Volume. Analytical Chemistry. 1999;71(15):3292-3296.

CAPLUS abstract of Krohkin et al. Modified silica as a stationary phase for ion chromatography. Journal of Chromatography A. 1995;706:93-8.

Chan, et al. Microfabricated Polymer Devices for Automated Sample Delivery of Peptides for Analysis by Electrospray Ionization Tandem Mass Spectrometry. Analytical Chemistry. 1999;71(20):4437-4444.

Chiem, et al. Microchip systems for immunoassay: an integrated immunoreactor with electrophoretic separation for serum theophylline determination. Clinical Chemistry.1998;44(3):591-598.

Chiem, et al. Room temperature bonding of micromachined glass devices for capillary electrophoresis. Sensors and Actuators. 2000;B63(3):147-152.

Ericson, et al. Electroosmosis- and Pressure-Driven Chromatography in Chips Using Continuous Beds. Analytical Chemistry. 2000;72(1):81-87.

Figeys, et al. A Microfabricated Device for Rapid Protein Identification by Microelectrospray Ion Trap Mass Spectrometry. Analytical Chemistry. 1997;69(16):3153-3160.

Figeys, et al. An Integrated Microfluidics-Tandem Mass Spectrometry System for Automated Protein Analysis. Analytical Chemistry. 1998;70(18):3728-3734.

Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.

Figeys, et al. Nanoflow Solvent Gradient Delivery from a Microfabricated Device for Protein Identifications by Electrospray Ionization Mass Spectrometry. Analytical Chemistry. 1998;70(18):3721-3727.

Kopp, et al. Chemical Amplification Continuous-Flow PCR on a Chip. Science. 1998;280:1046-1048.

Lazar, et al. Subattomole-Sensitivity Microchip Nanoelectrospray Source with Time-of-Flight Mass Spectrometry Detection. Analytical Chemistry. 1999;71(17):3627-3631.

Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.

Li, et al. Rapid and sensitive separation of trace level protein digests using microfabricated devices coupled to a quadrupole - time-of-flight mass spectrometer. Electrophoresis. 2000;21:198-210.

Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.

Licklider, et al. A Micromachined Chip-Based Electrospray Source for Mass Spectrometry. Analytical Chemistry. 2000;72(2):367-375.

Ocvirk, et al. High Performance Liquid Chromatography Partially Integrated onto a Silicon Chip. Analytical Methods and Instrumentation. 1995;2:74-82.

Ocvirk, et al. Optimization of confocal epifluorescence microscopy for microchip-based miniaturized total analysis systems. The Analyst. 1998;123:1429-1434.

Ramsey, et al. Generating Electrospray from Microchip Devices Using Electroosmotic Pumping. Analytical Chemistry. 1997;69(6):1174-1178.

Seifar, et al. Capillary electrochromatography with 1.8-mum ODS-modified porous silica particles. Journal of Chromatography. 1998; A808:71-77.

Spiering, et al. Novel microstructures and technologies applied in chemical analysis techniques. 1997 International Conference on Solid-State Sensors and Actuators. 1997;1:511-514.

Van Der Moolen, et al. A Micromachined Injection Device for CZE: Application to Correlation CZE. Analytical Chemistry. 1997;69(20):4220-4225.

Van Der Moolen, et al. Correlation Capillary Zone Electrophoresis, a Novel Technique to Decrease Detection Limits. Chromatographia. 1995;40(7/8):368-374.

Wen, et al. Microfabricated isoelectric focusing device for direct electrospray ionization-mass spectrometry. Electrophoresis. 2000;21:191-197.

Wright, et al., Behavior and Use of Nonaqueous Media without Supporting Electrolyte in Capillary Electrophoresis and Capillary Electrochromatography. Analytical Chemistry. 1997;69(16):3251-3259.

Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.

Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.

Xue, et al. Multichannel Microchip Electrospray Mass Spectrometry. Analytical Chemistry. 1997;69(3):426-430.

Zhang, et al. A Microdevice with Integrated Liquid Junction for Facile Peptide and Protein Analysis by Capillary Electrophoresis/Electrospray Mass Spectrometry. Analytical Chemistry. 2000;72 5):1015-1022.

Zhang, et al. Microfabricated Devices for Capillary Electrophoresis-Electrospray Mass Spectrometry. Analytical Chemistry. 1999;71(15):3258-3264.

International search report and written opinion dated Mar. 24, 2011 for PCT Application No. US2010/058227.

U.S. Appl. No. 12/026,510, filed Feb. 5, 2008, Jovanovich et al.
U.S. Appl. No. 12/526,015, filed Nov. 3, 2010, Jovanovich et al.
U.S. Appl. No. 12/815,685, filed Jun. 15, 2010, Jovanovich et al.
U.S. Appl. No. 12/820,390, filed Jun. 22, 2010, Harrison et al.
U.S. Appl. No. 12/845,650, filed Jul. 28, 2010, Jovanovich et al.
U.S. Appl. No. 12/852,370, filed Aug. 6, 2010, Harrison et al.
U.S. Appl. No. 12/949,623, filed Nov. 18, 2010, Kobrin et al.
Japanese Office Action dated Apr. 27, 2010 for Application No. JP2001-540363.
U.S. Appl. No. 12/026,510, filed Feb. 5, 2008, Jovanovich et al.
Japanese Office Action dated Dec. 21, 2010 for Application No. JP2001-540363.
MillGat pump user manual, version 2.12, published 2005, pp. 1-28.

* cited by examiner

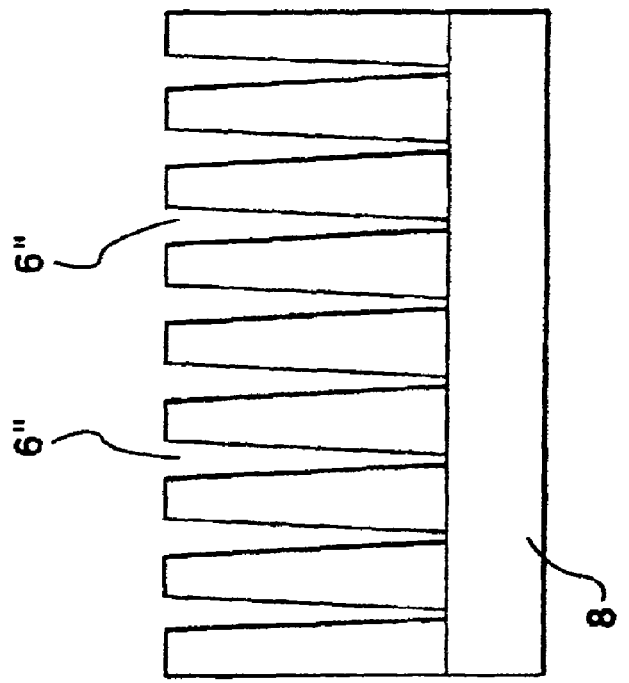
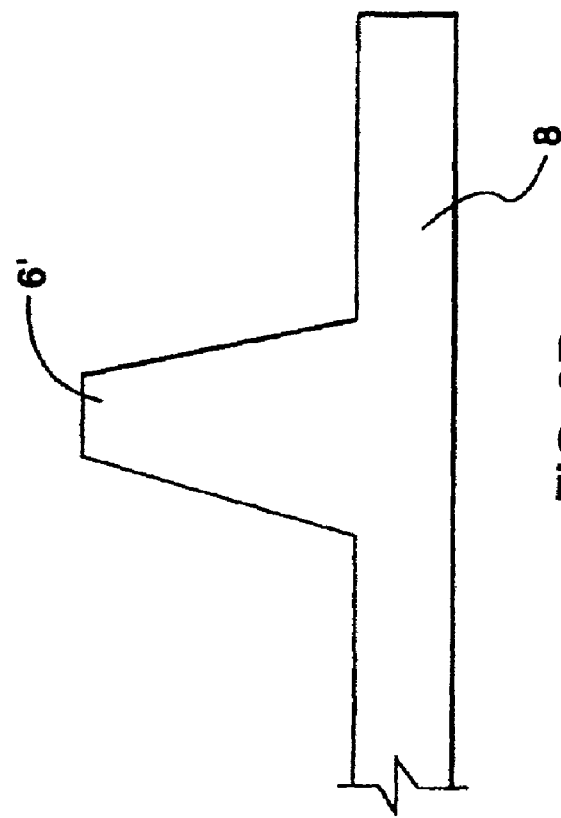

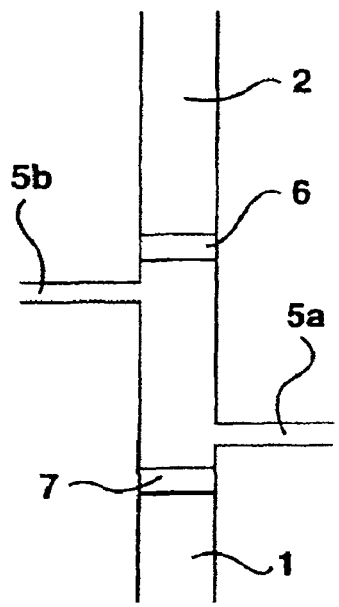
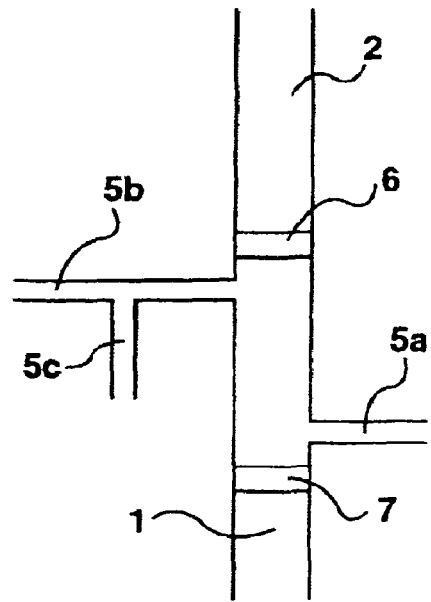
FIG. 8A            FIG. 8B
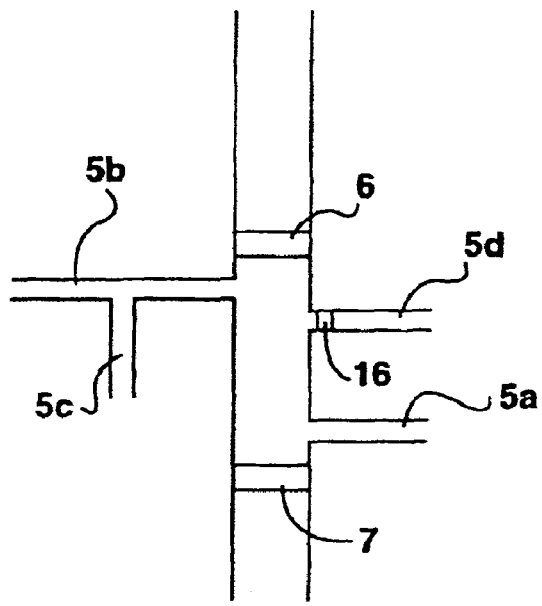
FIG. 8C

US 8,034,628 B2

APPARATUS AND METHOD FOR TRAPPING BEAD BASED REAGENTS WITHIN MICROFLUIDIC ANALYSIS SYSTEMS

CROSS-REFERENCE TO RELATED APPLICATIONS

This application is a Continuation application and claims priority to application Ser. No. 11/955,902, filed Dec. 13, 2007, now abandoned, which is a Continuation application of Ser. No. 10/148,425, filed Nov. 4, 2002, now U.S. Pat. No. 7,312,611, which claims the benefit of PCT application no. PCT/CA00/01421, filed Nov. 27, 2000; and Canadian application serial no. 2,290,731 filed Nov. 26, 1999; the entire contents of which are incorporated herein by reference.

FIELD OF THE INVENTION

The present invention relates generally to microfluidic analysis systems, and more specifically to micro-Total Analysis Systems (μ-TAS), for performing liquid phase analysis at a miniaturized level.

BACKGROUND INFORMATION

Recent developments in the field of micro-Total Analysis Systems (μ-TAS) have led to systems that perform chemical reactions, separation and detection at a miniaturized level on a single microchip [see, for example, Harrison, D. J.; Fluri, K.; Seiler, K.; Fan, Z.; Effenhauser, C. S.; and Manz, A., *Science* 1993, 261, 895-897. Harrison, D. J.; and van den Berg, E.; Eds., *Micro Total Analysis Systems '98, Proceedings of the μTAS '98 Workshop* (Kluwer: Dordrecht, 1998). Coyler, C. L.; Tang, T.; Chiem, N.; and Harrison, D. J., *Electrophoresis* 1997, 18, 1733-1741].

Most prior art microfluidic devices are based on conventional open tubular flow designs and solution phase reagents. While the functionality of these devices has continued to increase, one key feature that is presently lacking in these prior art devices is the ability to effectively incorporate on-chip packed reactor beds, for introduction of packing materials with immobilized reagents or stationary phases. While a few attempts have been made to employ packed reactor beds in some prior art designs, the difficulty of packing portions of a complex microfluidic manifold with packing material (such as microscopic beads) has so far hindered the effective utilization of these reagent delivery vehicles within microfluidic devices. (The difficulty of packing has been well recognized by practitioners in the field. See, for example, Ericson, C; Holm, J.; Ericson, T.; and Hjertén, S., *Analytical Chemistry.*)

In one prior art example, a packed bed chromatographic device with a bead trapping frit was fabricated in a silicon substrate [Ocvirk, G., Verpoorte, E., Manz, A., Grasserbauer, M., and Widmer, H. M. *Analytical Methods and Instrumentation* 1995, 2, 74-82]. However, the packing material in this prior art design could not be readily packed or exchanged, thus limiting its utility.

Several authors have also described the difficulties associated with reproducibly fabricating frits for retaining packing material in conventional capillaries [Boughtflower, R. J.; Underwood, T.; Paterson, C. J. *Chromatographia* 1995, 40, 329-335. Van den Bosch, S. E.; Heemstra, S.; Kraak, J. C.; Poppe, H. J. *Chromatogr. A* 1996, 755, 165-177. Colon, L. A.; Reynolds, K. J.; Alicea-Maldonado, R.; Fermier, A. M. *Electrophoresis* 1997, 18, 2162-2174. Majors, R. E. *LC-GC* 1998, 16, 96-110]. The frits used in conventional systems are prepared using time and labor intensive procedures, the most commonly used method involving the use of pure silica gel, wetted down with aqueous sodium silicate. The frit is made by first tapping a capillary end into a paste made from silica and aqueous sodium silicate. The resulting plug of silica is then heated to make a frit. Current construction methods do not produce high yields of useable frits.

Furthermore, using fits produced by prior art methods of construction often leads to the formation of undesirable bubbles. [Altria, K. D.; Smith, N. W.; and Turnbull, C. H., *Chromatographia*, 46 (1997) 664. Majors, R. E., *LC-GC*, 16 (1998) 96.] Bubbles cause discontinuity within a column, hindering solution flow and ultimately preventing separation from occurring. The bubbles are thought to arise from a change in electroosmotic flow (EOF) velocity caused by moving from a bead trapping frit into an open capillary. The formation of bubbles, which have been observed to increase at higher voltages, also limits the amount of voltage that can be applied across the capillary, thereby limiting column length, separation efficiency, and speed of analysis.

Developing a functional on-chip packed reactor bed design which overcomes the limitations in the prior art would significantly enhance the range of the microfluidic toolbox and extend the number of applications of such devices.

SUMMARY OF THE INVENTION

Generally, the present invention provides an on-chip packed reactor bed design using one or more weir structures that allow for an effective exchange of packing materials (beads for example) at a miniaturized level. The present invention extends the function of microfluidic analysis systems to new applications. For example, the packed reactor bed formed according to the present invention allows on chip solid phase extraction (SPE) and on-chip capillary electrochromatography (CEC), as explained in detail further below. The design can be further extended to include, for example, integrated packed bed immuno or enzyme reactors.

In a first aspect, the present invention provides a method of treating a sample within a microfluidic analysis system, comprising the steps of:

a) providing a main channel having a trapping zone suitable for trapping packing material;

b) providing a slurry of a reagent treated packing material prepared in a solution having a predetermined composition of a solvent;

c) inducing a flow of said packing material into said trapping zone through a flow channel connected to said trapping zone so as to load said trapping zone and form a packed bed of said packing material;

d) flowing a sample containing analytes through said packed bed, said reagent treating the sample, whereby the sample leaving the trapping zone has an altered analyte composition.

In one embodiment, the method further comprises the step of:

e) adjusting the composition of the solvent, so as to affect the aggregation of said packing material and the stabilization of the packed bed.

In another embodiment, step b) comprises providing packing material comprising porous beads.

In another embodiment, said porous beads are selected to have a diameter in the range from about 0.7 to about 10.0 μm.

In yet another embodiment, said porous beads are selected to have a diameter in the range from about 1.5 to about 4.0 μm.

In another embodiment, said solvent is acetonitrile, and step e) comprises adjusting the concentration level to less than about 50% to stabilize the packed bed.

In another embodiment, said solvent is acetonitrile, and step e) comprises adjusting the concentration level to less than about 30% to stabilize the packed bed.

In another embodiment, the method further includes the steps of adjusting the concentration level to above 50% to destabilize the packed bed, and reversing the flow in step c) so as to unload said trapping zone.

In another embodiment, the method further includes the step of repeating step c) so as to reload said trapping zone, and readjusting the concentration level to restabilize the packed bed.

In yet another embodiment, the method further comprises the steps of:
before step c), adding a neutral surfactant to said packing material so as to inhibit aggregation; and after step c), removing the neutral surfactant to promote aggregation.

In another embodiment, the method further comprising the steps of:
after step c) introducing a polymerizable agent into the flow channel and polymerizing said agent, so as to stabilize the packed bed.

In yet another embodiment, step d) comprises applying a fluid force to induce the flow of said packing material.

In another embodiment, said packing material comprises at least some electrically charged particles and step d) comprises applying a voltage potential to induce the flow of said packing material.

In another embodiment, said packing material comprises at least some particles susceptible to a magnetic field and step d) comprises applying a magnetic field to induce the flow of said packing material.

In another embodiment, the method further includes the step of providing a hook structure at the connection point between said flow channel and said trapping zone, so as to prevent direct line-of-sight entry of said packing material, thereby to promote even packing.

In another aspect, the present invention provides a method of trapping bead based reagents within a microfluidic analysis system, comprising the steps of:
a) providing a main channel having a trapping zone suitable for trapping bead based packing material;
b) providing a slurry of a reagent treated beads prepared in a solution having a predetermined composition of a solvent;
c) inducing a flow of said beads into said trapping zone through a flow channel connected to said trapping zone so as to load said trapping zone and form a packed bed of said beads; and
d) adjusting the composition of the solvent, so as to affect the aggregation of said packing material and the stabilization of the packed bed.

In a further aspect, the present invention provides a microfluidic analysis system, comprising:
a) a substantially planar substrate having an upper surface;
b) at least one main channel formed into said upper surface, said main channel having first and second ends and a defined direction of flow in use;
c) a cover plate arranged over said planar substrate, said cover plate closing off said channel from above; and
d) a first weir formed across said main channel and between said first and second ends of said channel, said first weir providing at least one flow gap to allow, in use, at least some fluid to flow past said first weir while trapping packing material having constituent particles that are generally larger than said flow gap.

In one embodiment, the system further comprises at least one side channel formed into the upper surface of said planar substrate, said side channel being connected at a first end to said main channel at a location upstream from said first weir, and at a second end to a reservoir, said side channel providing a higher flow resistance than said main channel.

In another embodiment, the system further comprises a second weir located upstream from said connected first end of said side channel, said first and second weirs forming a chamber therebetween, said second weir providing at least one flow gap to allow, in use, at least some fluid to flow past said second weir while trapping said packing material within said chamber.

In another embodiment, each side channel connection to said main channel is provided with a hook structure curved to one side whereby, in use, packing material is sprayed into said chamber to facilitate even packing.
direct line-of-sight entry of packing material from said side channel into said chamber and forms a chamber mouth to one side of said hook structure.

In another embodiment, said flow gaps comprise a generally uniform gap between said cover plate and the top of said weirs.

In yet another embodiment, said flow gaps comprise a plurality of substantially vertical gaps in said weirs.

In another embodiment, said system is formed entirely on a single microfluidic chip.

In another embodiment, the present invention provides a method comprising, providing a non-conductive substrate and effecting an electrokinetic flow by applying a relatively high voltage at said second end of said main channel and at said reservoir, said reservoir containing packing material, and providing a relatively low voltage at said first end of said main channel, so that packing material flows from said reservoir into said main channel and is trapped against said first weir.

In one embodiment, the packing material is removed from said main channel by providing a relatively high voltage at said first and second ends of said main channel while providing a relatively low voltage at said reservoir.

In another aspect, the present invention provides a method comprising, effecting a pressure driven flow by providing a relatively high pressure at said second end of said main channel and at said reservoir, said reservoir containing packing material, and providing a relatively low pressure at said first end of said main channel, so that packing material flows from said reservoir into said main channel and is trapped against said first weir.

In one embodiment, the packing material is removed from the said main channel by providing relatively high pressure at said first and second ends of said main channel while providing relatively low pressure at said reservoir.

In another embodiment, the method comprises providing a non-conductive substrate and effecting an electrokinetic flow by applying a relatively high voltage at said reservoir, said reservoir containing packing material, and providing relatively low voltages at said first and second ends of said main channel, so that packing material flows from said reservoir into said chamber and is trapped by said first and second weirs.

In another embodiment, the packing material is removed from the chamber by reversing said electrokinetic flow.

In another aspect, the present invention provides a method of packing the chamber in a microfluidic analysis system comprising, effecting a pressure driven flow by providing a relatively high pressure at said reservoir, said reservoir containing packing material, and providing relatively low pressure at said first and second main reservoirs, whereby, packing material flows from said packing material reservoir into said chamber and is trapped by said first and second weirs.

In another embodiment, the packing material may be removed from the chamber by reversing said pressure driven flow.

In another embodiment, the method comprises providing magnetically charged packing material, and effecting a magnetically driven flow by providing a magnetically attractive force in the chamber, whereby, the packing material enters the chamber and is trapped by said first and second weirs.

In another embodiment, the packing material may be removed from the chamber by reversing said magnetic force in said chamber.

In any of the above embodiments, the packing material may comprise porous beads.

In another embodiment, the beads may be generally spheroid.

In another embodiment, the beads are initially suspended in a buffer solution.

In another embodiment, the buffer solution is an organic solvent miscible with water.

In another embodiment, the organic solvent is acetonitrile with a concentration level of up to 50%.

BRIEF DESCRIPTION OF THE DRAWINGS

For a better understanding of the present invention, and by way of example, reference will now be made to the accompanying drawings, which show preferred embodiments of the present invention in which:

FIGS. 2B and 2C show a side view and end view, respectively, of an alternative embodiment of a weir according to the present invention;

FIGS. 8A-8C show top plan views of alternative embodiments of a microfluidic device according to the present invention;

DETAILED DESCRIPTION OF THE INVENTION

Figure 1A:
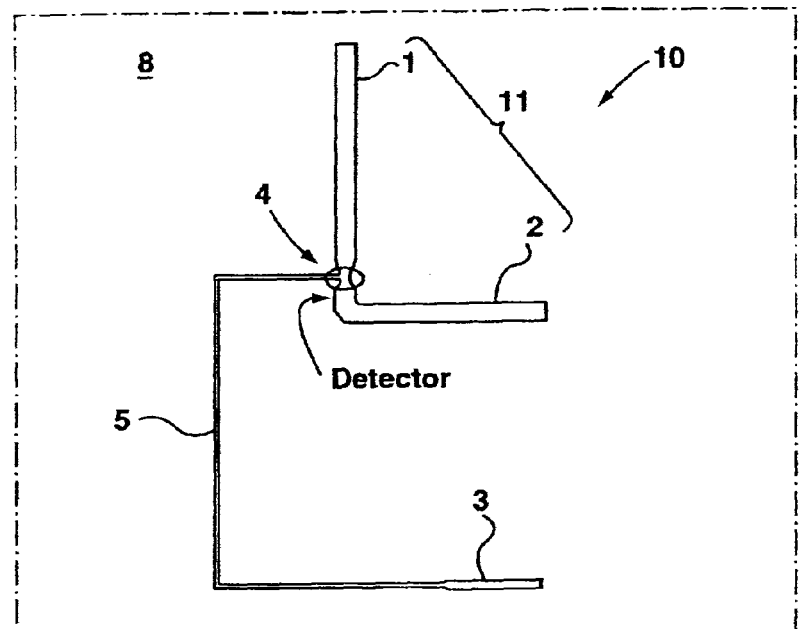
FIG. 1A shows a top plan view of a microfluidic device according to the present invention.

As explained above, the present invention is designed to provide a convenient system and method of trapping packing materials (such as beads) on-chip, and of effectively packing and unpacking the trapping zones, to provide a functional on-chip packed reactor bed which significantly extends the number of applications of microfluidic analysis devices.

One such extended application facilitated by the present invention is on-chip sample preconcentration by solid phase extraction (SPE). In microfluidic analysis, SPE is often required to overcome detection limit problems, or to eliminate a potential interferent. To date, preconcentration within microchips has been performed by sample stacking using "isoelectric focusing" [Jacobson, S. C. and Ramsey, M. Electrophoresis 1995, 16, 481 486]. Advantageously, unlike sample stacking, SPE can be made selective for a particular analyte and does not require precise control of buffer concentrations. For SPE the amount of preconcentration is limited by the preconcentration time, which makes it more flexible than sample stacking. The SPE of an analyte can be beneficial not only for analyte preconcentration, but also for removing other impurities or changing solvent conditions. While the coupling of SPE with microfluidic devices has been accomplished [Figeys, D. and Aebersold, R. Anal. Chem. 1998, 70, 3721 3727], the SPE component in these prior art devices have been made in a capillary or similar cartridge external to the chip, thus resulting in a more complex and more expensive system. The present invention is designed to overcome this prior art limitation by facilitating an on-chip SPE component.

As realized by the present inventors, an integrated, on chip SPE component is ultimately easier to manufacture, does not require low dead volume coupling to the chip, and eliminates sample handling losses or contamination problems arising from the off chip sample manipulation required in the prior art. It is anticipated that routine incorporation of SPE onto a chip, as facilitated by the present invention, will reduce problems with on chip detection limits and will improve the range of sample preparation steps which can be integrated.

Another extended application facilitated by the present invention is on-chip capillary electrochromatography (CEC). CEC has recently received significant attention due to the fact that it combines the separation power of both liquid chromatography and capillary electrophoresis. To date the difficulty associated with packing chromatographic material within devices has focused most previous chromatographic efforts upon prior art open channel methods [Manz. A., Miyahara, Y., Miura, J., Watanabe, Y., Miyagi and H. Sato, K., *Sens. Actuators* 1990, B1, 249 255; Jacobson, S. C., Hergenröder, R., Koutny, L. B. and Ramsey, J. M. Anal. Chem. 1994, 66, 2369 2373; Kutter, J. P., Jacobson, S. C., Matsubara, N. and Ramsey, J. M. *Anal. Chem.* 1998, 70, 3291 3297; He, B., Tait, N. and Regnier, F. Anal. Chem. 1998, 70, 3790 3797]. In the prior art, open channel method devices with channel widths of 2 μm or less were required to improve mobile phase transfer in open columns leading to other practical considerations such as clogging and a short path length for detection. There were also problems with the reproducibility and the cost of stationary phase coating in such structures.

As realized by the inventors, on-chip packed bed chromatography according to the present invention has the benefit of providing low mobile phase mass transfer, and makes available a wide variety of stationary phases. In this case, the use of an off chip prepared stationary phase offers the advantage that it eliminates the need for coating the chip and allows for optimization of the stationary phase preparation.

Yet another extended application facilitated by the present invention is providing on-chip bead based immunoassay and enzyme based assays. These applications are described further below.

EXAMPLE

To illustrate the present invention by way of example, the inventors conducted a series of experiments, which are described here.

Chip Design

Figure 1B:
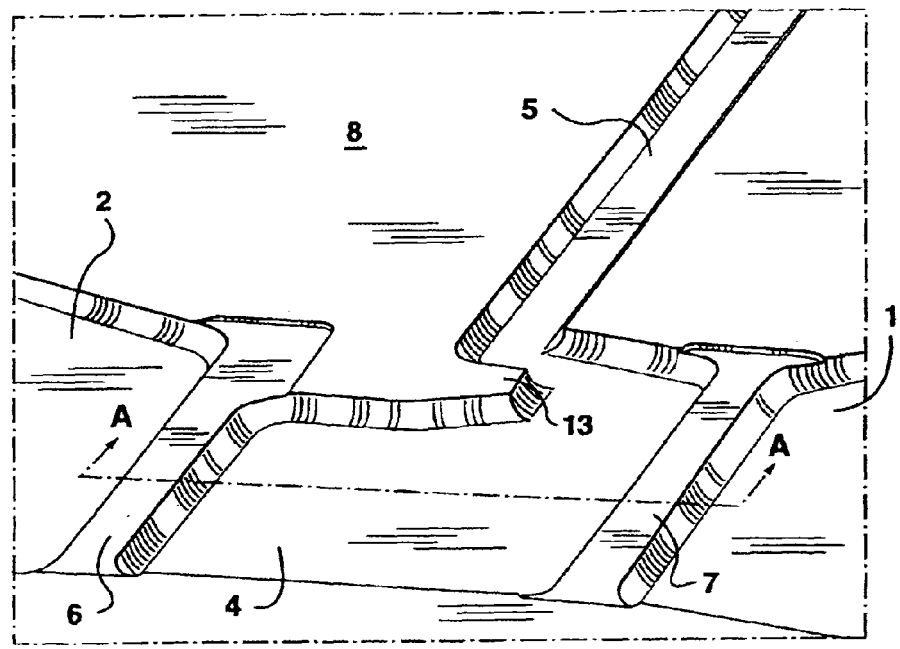
FIG. 1B shows an enlarged perspective view of a chamber in which packing materials (such as beads) are trapped.

FIGS. 1A and 1B show a microfluidic device 10 as used in these experiments. The device 10 comprises a main channel 11 formed into the top surface of a substrate 8, and the main channel 11 is separated by a chamber 4, also formed into the substrate 8. Two branches of the main channel 11, as separated by the chamber 4, are further identified as main reservoirs 1 and 2. The chamber 4 is connected to a packing material reservoir 3 by a narrow side channel 5. The packing material reservoir and the narrow side channel 5 are also formed into the substrate 8. FIG. 1B shows an enlarged image of the chamber 4 obtained with a scanning electron microscope (Jeol X Vision JSM6301FXV, Peabody, Mass.). The chamber 4 is formed by providing two weirs 6, 7 formed across the main channel 11 at a relatively narrow portion of the main channel 11 (FIG. 1A). As can be seen from FIG. 1B, the weirs 6, 7 are not as high as the main channel 11 is deep, so that some fluid is allowed to flow over the weirs 6, 7 as explained below. The device 10 was prepared in Corning 0211 glass by the Alberta Microelectronic Corporation (Edmonton, AB), using known chemical etching procedures [Fan, Z. H.; Harrison, D. J. *Anal. Chem.* 1994, 66, 177 184]. It is noted that this substrate material is non-conductive, but if other than electrokinetic forces are being used (as detailed further below), then the substrate material may be semiconducting or conducting. Two photomasks were required to create device 10: a first photomask was used to etch the tops of the weirs 6, 7 to a depth of approximately 1 µm; and a second photomask was used to etch the channels 5, 11 to a depth of approximately 10 µm.

Figure 2A:
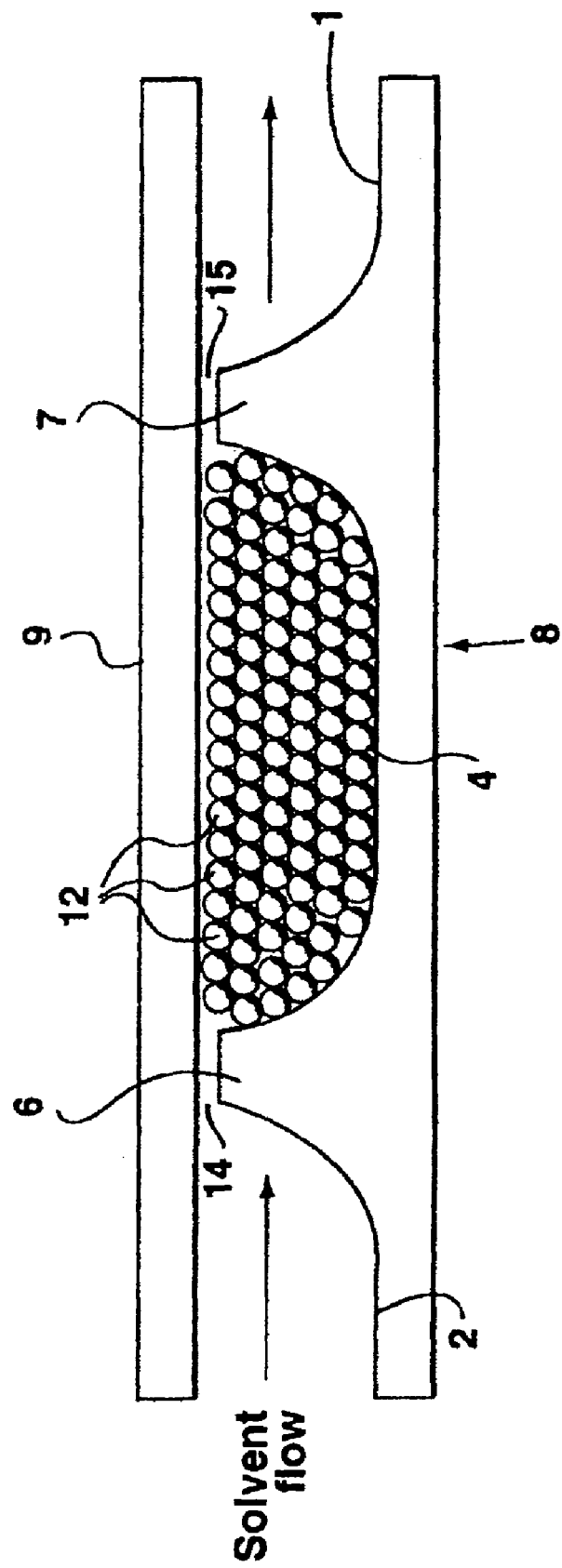
FIG. 2A shows a cross-sectional view of the chamber shown in FIG. 1B taken along line A-A, and further shows packing material (beads) which are packed into the chamber and which are retained by a cover plate.

FIG. 2A shows a cross-sectional view of the weirs 6, 7 which are not as high as the channel 11 (main reservoirs 1, 2) is deep, and thus small flow gaps 14, 15 are provided between the top of the weirs 6, 7 and a cover plate 9 (not shown in FIG. 1A or 1B) which is placed on top of the substrate 8, thereby closing off the chamber 4, channels 5, 11 and reservoirs 1, 2, 3. As can be seen in FIG. 2A, the beads 12 are generally larger than the flow gaps 14, 15 and therefore cannot escape from the chamber 4.

FIGS. 2B and 2C show a side view and an end view, respectively, of an alternative embodiment of a weir 6' in which substantially vertical notches 6" are provided so that the weir 6' provides less flow impedance. The vertical notches 6" should be narrow enough that no beads can pass through them (i.e. they should be at least about 10% smaller than the smallest bead diameter).

Solutions and Reagents

Various solutions and reagents were used in these experiments. Acetonitrile (BDH, Toronto, ON) was filtered through a 0.45 µma Nylon 6,6 filter (Altech, Deerfield, Ill.) prior to use. Otherwise, the acetonitrile was used as received, with no added electrolyte. Also, 50 mM potassium phosphate (pH 7.0) and ammonium acetate (pH 8.5) buffers were prepared in ultra-pure water (Millipore Canada, Mississauga, ON). A 1:1 (v/v) mixture of acetonitrile and buffer was prepared. A stock solution of 0.10 mM, 4,4 difluoro 1,3,5,7,8 penta methyl-4-bora-3a,4a-diaza-s-indacene, BODIPY 493/503 (Molecular Probes, Eugene, Oreg.) was prepared in HPLC grade methanol (Fisher, Fair Lawn, N.J.). A 1 mM stock solution of fluorescein di sodium salt (Sigma) was prepared in phosphate buffer. Both stock solutions were then diluted in the 50 mM phosphate and 50 mM ammonium acetate buffers to give 1.0 µM solutions, which were then diluted to 1.0 nM. This 1.0 nM solution served as the sample for preconcentration and electrochromatography. All aqueous (buffer and sample) solutions were filtered through a cellulose acetate syringe filter (0.2 µm pore size) (Nalgene, Rochester, N.Y.) prior to use.

Packing Material

One suitable packing material used in these experiments comprised a reverse phase chromatographic stationary resin. The resin was Spherisorb ODS1 (Phase Separations, Flintshire, UK), a porous C-18 resin whose particles ranged from 1.5 to 4.0 µm in diameter, as determined by scanning electron microscopy (ODS beads 12). A slurry of approximately 0.003 g/mL of ODS1 was prepared in acetonitrile. This slurry was used to supply the packing material reservoir 3, to subsequently pack the chamber 4.

Certain solvent and additive combinations were found to help the packing material stay in the packed chambers. For example, if ODS beads are introduced in acetonitrile they flow readily, while subsequently switching to an aqueous or predominately aqueous solvent causes the beads to aggregate and become trapped within the chamber. With ODS beads up to 30% acetonitrile could be present in the aqueous solution without disrupting the aggregation observed to the point of destabilizing the packed bed. Up to 50% acetonitrile could be present with only modest loss in aggregation and weak destabilization of the bed. As another example protein G or protein A coated beads formed aggregates in aqueous solution, which made it hard to introduce them into the trapping zone. However, the addition of a neutral surfactant such as Tween 20 or Brij 35 (both are trademarks) prevented such aggregation and allowed the beads to be introduced. Conversely, subsequent removal of the surfactant form the aqueous solvent resulted in aggregation and enhanced stability of the trapped bed. The following trend was observed: when using non polar or partially non polar bead phases (for example, ODS and protein coated beads) lowering the surface tension of the solvent from that of water or buffered water, by the addition of organic additives such as organic solvents or surfactants, reduced the tendency to aggregate. Conversely reducing or eliminating materials with lower surface tension from aqueous solution increased the tendency to lock the beads in place on the bed, creating a "solvent lock" method to enhance bead trapping within these devices. Other organic solvents other than acetonitrile, miscible with water may also be used for these purposes, such as methanol, ethanol, dimethylsulfoxide, propylene carbonate, etc. Charged surfactants may also be used instead of neutral surfactants, so long as they are compatible with the proteins that may be present on the beads or in the sample.

Magnetic beads used for magnetic packing may comprise Abebaw-protein "A" coated beads: composition 36-40% magnetite dispersed within a copolymer matrix consisting of styrene and divinyl benzene (Prozyme, Calif.) Also, Guifeng-oligo (dT)25 coated beads may be used for the isolation of mRNA. The beads have an even dispersion of magnetic material ($Fe_2O_3$ and $Fe_3O_4$) through out the bead. The beads are coated with a polystyrene which encases the magnetic material (Dynal, Oslo, Norway).

Instrumentation

Various instruments were used in conducting the present experiments. As these instruments and their operation are well known to those skilled in the art, only a brief description is provided, and the instruments are not shown in the figures.

A power supply and relay system used to control the electrophoretic voltages necessary for bead packing and all liquid handling on chip has been described previously [Fluri, K., Fitzpatrick, G., Chiem, N. and Harrison, D. J. *Anal. Chem.* 1996, 68, 4285-4290]. LabVIEW programs (National Instruments, Austin, Tex.), were written for computer control of the voltage system and for data acquisition.

A laser induced fluorescence detection system used in this experiment consisted of a 488 nm argon ion laser (Uniphase, San Jose, Calif.), operated at 4.0 mW, and associated focusing optics [Manz. A., Miyahara, Y., Miura, J., Watanabe, Y., Miyagi, H. and Sato, K. Sens. Actuators 1990, B1, 249 255] (Melles Griot, Irvine, Calif.). Fluorescence emitted from the BODIPY sample (as described above) was collected by a 25×, 0.35 NA microscope objective (Leitz Wetzlar, Germany). The images were observed with a SONY CCD IRIS camera. Alternatively a 530 nm emission filter and a photo multiplier tube (PMT) (R1477, Hamamatsu, Bridgewater, N.J.) were used as a detector positioned so that the narrow channel 5 between the chamber 4 and packing material reservoir 3 could be monitored. Data was collected from the section of main channel 11 just next to the chamber 4. The weir 6 was just out of the field of view. The PMT was biased at 530 V while the PMT signal was amplified, filtered (25 Hz Butterworth) and sampled at a frequency of 50 Hz.

The fluorescence of the buffer, acetonitrile, and 1.0 nM BODIPY in both buffer and acetonitrile was measured using a Shimadzu RF 5301PC Spectrofluorophotometer.

While specific models and manufacturers have been provided for various instrumentation described above, it will be understood by those skilled in the art that any suitable, functional equivalent may be used.

Chip Operation

Referring back to FIGS. 1A and 1B, the narrow side channel 5 leading into the chamber 4 from packing material reservoir 3 was used to direct stationary phase packing material into the chamber 4 using electrokinetic pumping [Yan, C., U.S. Pat. No. 5,453,163, 1995; Knox, J. H. and Grant, I. H. Chromatographia 1991, 32, 317 328]. As mentioned above, the substrate 8 is non-conductive, which allows packing of the beads 12 using the electrokinetic pumping method.

The device 10 was not conditioned with any aqueous solutions prior to use. The chamber 4, channels 5, 11, and reservoirs 1, 2, 3 were first filled with acetonitrile. The chamber 4 was packed with ODS beads 12 (FIG. 2) by replacing the acetonitrile in packing material reservoir 3 with the ODS/acetonitrile slurry (described above), then applying positive high voltage at packing material reservoir 3 while holding main reservoirs 1 and 2 at ground. The voltage applied at packing material reservoir 3 was ramped from 200 V to 800 V over approximately 5 min to effect packing of chamber 4.

Once the chamber 4 was packed, a step gradient was performed to introduce aqueous solution to the main channel 11 and the ODS beads 12 in the chamber 4. A 1:1 (v/v) mixture of acetonitrile and buffer was placed in reservoirs 1 and 2. Acetonitrile replaced the slurry in packing material reservoir 3. A voltage was then applied to main reservoir 1 and was ramped from 200 V to 800 V, with packing material reservoir 3 biased at 400 V and main reservoir 2 grounded. After 2 to 5 min at 800 V, the acetonitrile/buffer mixture in reservoirs 1 and 2 was replaced with buffer, and the same voltage program repeated. The chamber 4 was monitored visually to ensure that the acetonitrile was completely replaced by buffer and that the packing material (beads 12) did not shift or unpack during this procedure. (The beads 12 could be seen to agglomerate as the acetonitrile was expelled, and the index of refraction change at the water/acetonitrile interface was clearly visible.) The experiments conducted are described in further detail below.

Experimental Results and Discussion

In order to conduct the experiments, it was necessary to pack the chamber 4 with packing material (beads 12), as shown in FIG. 2A.

The narrow side channel 5 shown in FIGS. 1A and 1B was made to be about 30 µm wide to supply packing material (beads 12) to the chamber 4. A sample could then be delivered from reservoir 2 (the inlet channel), across the chamber 4 and on towards main reservoir 1 (the outlet channel). The volume of the chamber 4 was 330 pL, while the volume of the outlet and inlet channels was 1.5×10 7 L and 4.1×10 8 L, respectively. The main channel 11 had much lower flow resistance than the side channel 5, in spite of the weirs 6, 7, given their relatively wide widths (580 µm tapering to 300 µm at the weirs) in comparison to the width of the narrow channel 5 (30 µm). The relative flow resistance in the device 10 was manipulated by the selection of the width dimensions for these channels 5, 11 in order to encourage flow between main reservoirs 1 and 2, rather than into the narrow bead introduction side channel 5 during sample loading and elution.

Reverse phase ODS beads 12 (as described previously) were used in the SPE device because of their extensive use for the chromatography of proteins, peptides and tryptic digests [Seifar, R. M.; Kok, W. T.; Kraak, J. C.; and Poppe, H. Chromatographia, 1997, 46, 131 136. Yan, C.; Dadoo, R.; Zhao, H.; Zare, R. N.; and Rakestraw, D. J., *Anal Chem.* 1995, 67, 2026 2029.] as well as other applications of SPE and CEC [Nielsen, R. G.; Riggin, R. M.; Rickard, E. C. J. Chromatogr. 1989, 480, 393 401. Hancock, W. S.; Chloupek, R. C.; Kirkland, J. J.; Snyder, L. R. *J. Chromatogr. A* 1994, 686, 31 43.]. Electrokinetic packing of conventional capillaries has been described previously, [Yan, C.; U.S. Pat. No. 5,453,163, 1995. Knox, J. H.; Grant, I. H. *Chromatographia* 1991, 32, 317 328.], and the inventors have adapted the method for the present invention.

As briefly explained earlier, the packing procedure involved applying a positive voltage (ramped from 200 800 V) to the packing material reservoir 3, while grounding main reservoirs 1 and 2. The applied voltage induced EOF to flow down the bead channel, carrying the beads into the cavity. An organic solvent was required to suspend the chromatographic beads 12 to prevent them from aggregating and plugging the narrow side channel 5. Studies have shown that capillaries filled with acetonitrile exhibit substantial electroosmostic flow [Wright, P. B.; Lister, A. S.; Dorsey, J. G. *Anal Chem.* 1997, 69, 3251 3259. Lister, A. S.; Dorsey, J. G.; Burton, D. E. J. High Resol. *Chromatogr.* 1997, 20, 523 528. Schwer, C.; Kenndler, E. *Anal. Chem.* 1991, 63, 1801 1807. Salimi Moosavi, H.; Cassidy, R. M. *Anal. Chem.* 1995, 67, 1067 1073.].

Figure 3A:
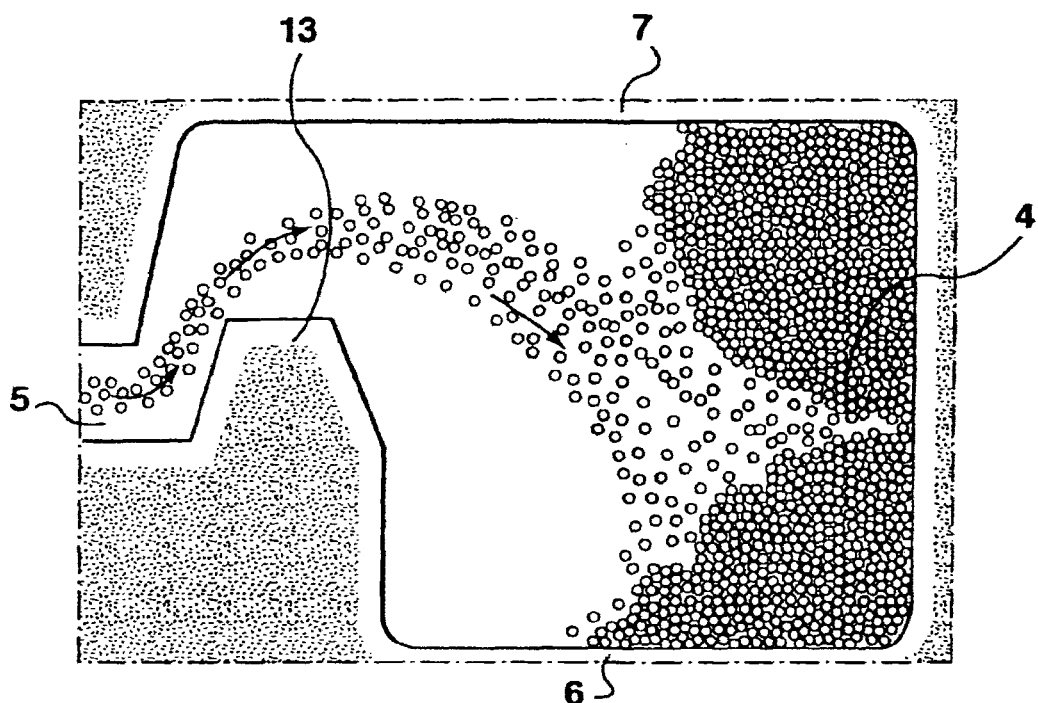
FIG. 3A shows an initial stage of packing material (beads) being packed into the chamber shown in FIGS. 1B and 2A.

As shown in FIG. 3A, at the early stages of packing, the beads 12 entering the chamber 4 contacted the weirs 6, 7 on either side of the chamber 4. As explained earlier, the beads 12 are unable to traverse the weirs 6, 7 because the distance from the top of the weirs 6, 7 to the bottom of the cover plate 9 (approximately 1.0 μm) is less than the diameter of the individual particles of the ODS beads 12 (approximately 1.5-4.0 μm).

Figure 3B:
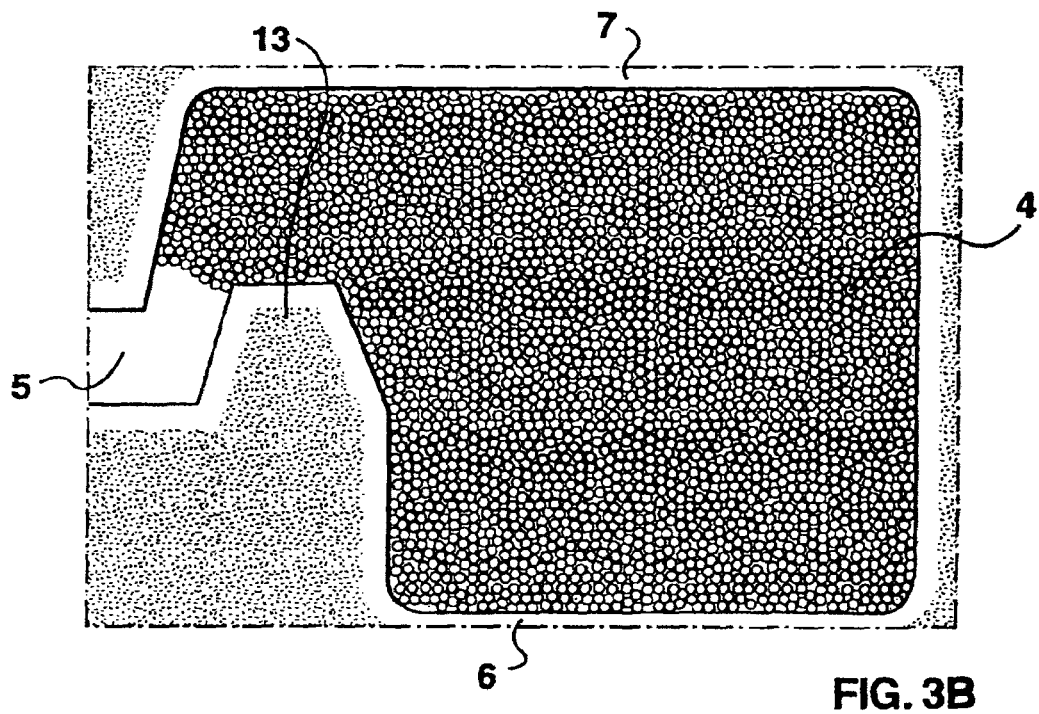
FIG. 3B shows the chamber of FIG. 3A after it has been completely filled with packing material (beads)

As shown in FIG. 3B, the chamber 4 continued to pack until it was entirely filled with chromatographic material. As discussed earlier, the difficulties associated with reproducibly fabricating frits for retaining packing material is well known. Importantly, the weir design used in the present invention circumvented this problem, and the electrokinetic packing of the beads provided an even distribution of beads throughout the chamber with no observable voids. In fact, the use of weir structures may ultimately eliminate the need for on column frit fabrication.

The weir design of the present invention allows electric fields to be applied across the trapping zone formed by two weirs, when filled with beads, in a range as high as 20,000 to 80,000 V/cm without bubble formation at the weir. Separations performed in devices with these weirs can use electric fields at least as high as 15,000 V/cm. The power dissipated across a weir can be as high as 3-7 W/m without the formation of bubbles. In contrast frits formed in conventional columns have at the best been reported to form bubbles at power dissipations above 0.6 W/m, and electric fields in the range of 150-600 V/cm are the best that have been reported without bubble formation.

It is possible to couple an external capillary to a chip and allow the weir to be used as the trapping element for the beads packed within the external electrochromatography capillary. This can be accomplished using a low dead volume coupling, such as described by Bings et al. (N. H. Bings, C. Wang, C. D. Skinner, C. L. Colyer, P. Thibeault, D. J. Harrison, *Anal. Chem.* 71 (1999) 3292 3296.) In this way the chip based weir can replace the frits normally formed within external capillaries, and allow higher electric fields to be used, improving speed and separation efficiency.

(It is noted here that it was also possible to pack the cavity by applying a vacuum at main reservoirs 1 and 2, although this was less convenient when electrokinetic flow was used for sample loading and elution.)

If for some reason the beads 12 did not pack as tightly as was desirable (as shown in FIGS. 2 and 3B) they were removed from the chamber 4 by simply reversing the voltages, and the packing procedure was then repeated. It is noted that once an aqueous solution was introduced to the chamber 4, the reverse phase beads 12 tended to aggregate and were more difficult to remove. However, subsequent removal was accomplished by flushing the aqueous solution out with acetonitrile, using either EOF or vacuum, or a combination of the two. Advantageously, the ability to effectively remove the beads 12 from chamber 4 allowed used chromatographic beads to be refreshed, or a more applicable material to be substituted.

Significantly, a design utilizing a hook structure 13 at the chamber entrance (FIGS. 1B and 3A) yielded the most favorable results in packing, enabling the chamber 4 to be packed and remain so after removal or alteration of voltages or vacuum. As seen from the figures, the side channel 5 connects to the chamber 4 via a chamber mouth 4 A in an asymmetric fashion, relative to the weirs 6, 7. Also, the hook structure 13 preferably obstructs direct line-of-sight entry of packing material from the side channel 5 into the chamber 4. Rather, the hook structure 13 forces packing material to enter the chamber 4 indirectly via the chamber mouth 4 A.

As explained earlier, during the packing step, the packing material reservoir 3 has a positive bias applied with reservoirs 1 and 2 grounded. The inventors believe that the hooked structure 13 causes electric field lines to follow a curved pathway into the cavity. Consequently, as the chromatographic beads 12 follow the electric field lines into the chamber mouth 4 A they appear to be "sprayed" as if from a snow blower (FIG. 3A), to become uniformly packed.

During the packing procedure the chamber 4 filled only to the beginning of the hook structure 13 (see FIG. 3B). Once filled, the beads were observed to flow down the sides and up the middle of the narrow side channel 5 (toward packing material reservoir 3) mimicking the solvent back flow generated in a closed electrophoretic system [Shaw, D. J. *Introduction to Colloid and Surface Chemistry*, $3^{rd}$ ed. Butterworths: London, 1980.]. In such a closed system, EOF is directed along the walls until it reaches the end of the chamber, where pressure causes the solution to reverse direction and flow back up the center of the bead introduction channel.

A key aspect of the hooked structure as shown is the asymmetric entrance into the trapping zone, which allows for better packing. A symmetric entrance means the entering beads can go to both weirs equally, which tends to lead to uneven or difficult packing. An asymmetric structure allows the beads to pack preferentially at one end of the trapping zone first and then build up in one direction from that location. The key role of the hook structure is to prevent line of sight outflow from the trapping zone during use of the packed bed.

Chambers constructed without an asymmetry in the entrance were not observed to pack as well as asymmetric entry designs. In these cases, packing material tended to fill the corners furthest from the entrance, but no additional material would enter the chamber. The inventors believe that, due to its symmetric design, this type of chamber exhibits solvent back flow, after it has filled to a certain extent. That is, the partially filled chamber may resemble a closed or restricted system. Such an occurrence would preclude the filling of the symmetric chamber with beads and is consistent with previously observed behavior, as explained by Shaw. Such behavior may account for the ability to fill symmetric structures on some occasions but less readily on others. In contrast, an asymmetric design, with or without a hook structure 13 guarding the entrance is less likely to experience back flow directly into the narrow bead introduction channel 5.

Solid Phase Extraction (SPE) On-Chip

Figure 4A:
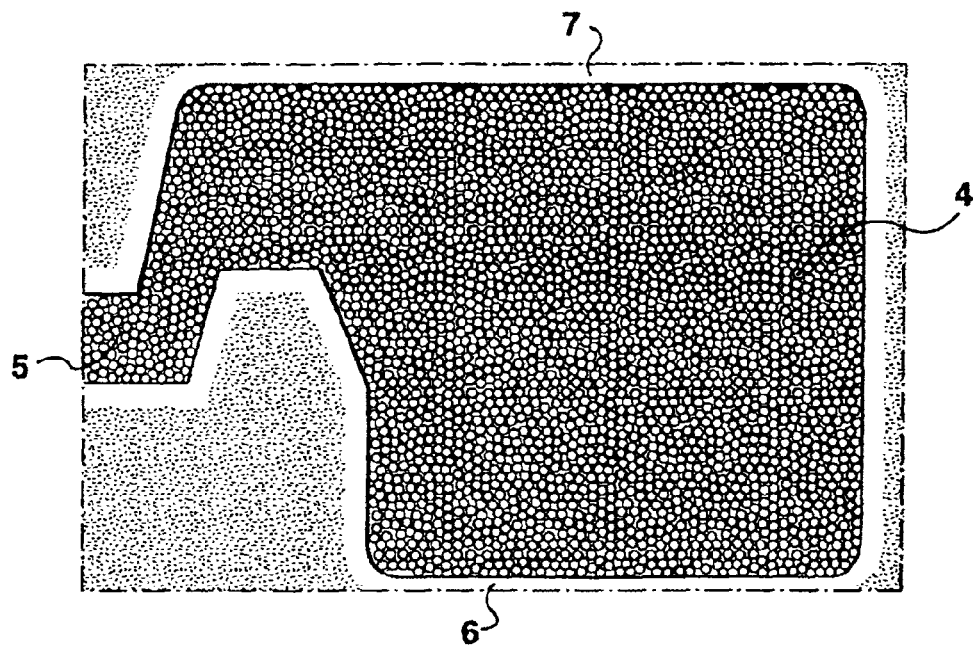
FIG. 4A shows an early stage of preconcentration of a 1.0 nM BODIPY solution at the weir/bed interface near the top of FIG. 4A.
Figure 4B:
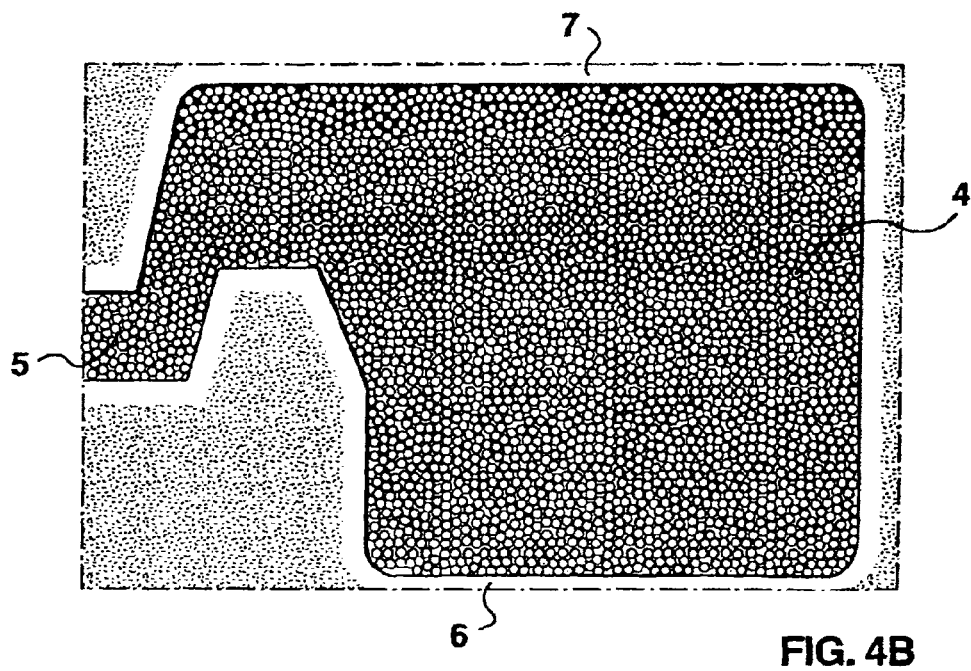
FIG. 4B shows a later stage of preconcentration of a 1.0 nM BODIPY solution at the weir/bed interface near the top of FIG. 4B.
Figure 5:
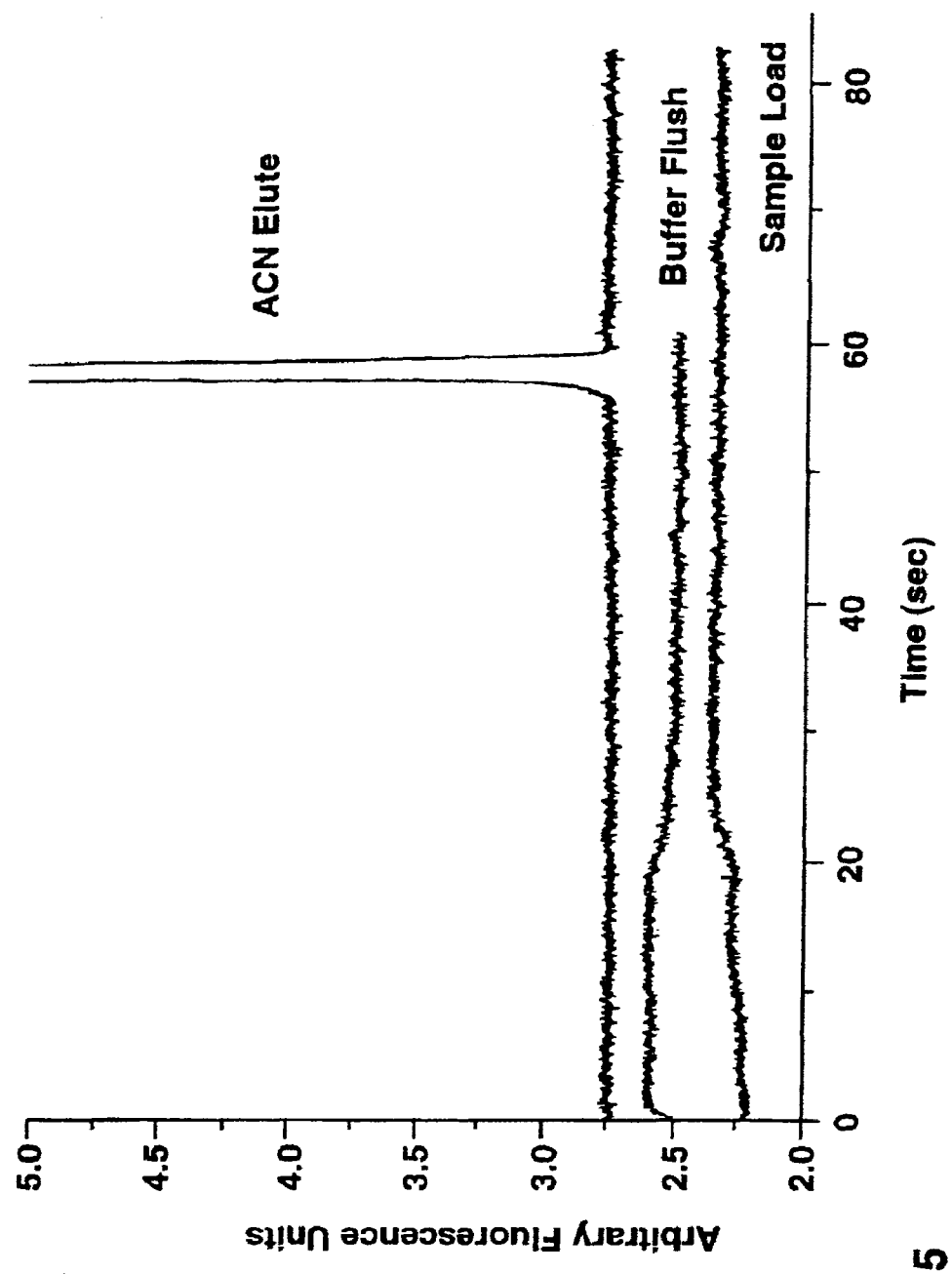
FIG. 5 shows a plot of fluorescence intensity vs. time, showing fluorescence of a first 1.0 NM BODIPY sample during loading, followed by a buffer flush, and then preconcentrated BODIPY during elution with acetonitrile (ACN)

As explained earlier, the present invention allows applications of microfluidic analysis systems to be extended. One such extension is facilitating SPE directly on-chip. Preconcentration is a valuable tool that can be used to enhance the sensitivity of microfluidic devices. To determine the ability of a packed SPE bed constructed on a microchip to preconcentrate an analyte, the inventors concentrated a 1.0 nM solution of BODIPY reagent from 50 mM phosphate buffer. Solution conditions utilized were similar to those used for protein and peptide analysis in HPLC CE systems. [Bushey, M. M.; Jorgenson, J. W. *Anal. Chem.* 1990, 62, 978 984. Castagnola, M.; Cassiano, L.; Rabino, R.; Rossetti, D. V. *J. Chromatogr.* 1991, 572, 51 58.] The BODIPY reagent, when diluted in aqueous buffer, exhibits a high affinity for ODS material and is an excellent fluorophore. The preconcentration and elution of the BODIPY reagent was carried out in four steps: equilibration of the SPE bed with buffer; sample introduction; buffer flush; and elution of analyte. Following rinsing of the packed bed with phosphate buffer, a solution of 1.0 nM BODIPY was placed in main reservoir 1, and +200 V was applied for 2 minutes, with main reservoir 2 grounded. The EOF (0.2 mm/sec, $1.2 \times 10^{-9}$ L/sec) flowed towards reservoir 2, carrying the BODIPY onto the SPE bed during the loading step. As shown in FIG. 4A, fluorescence of the absorbed BODIPY occurred initially at the first few layers of beads 12 only (near the top of the Figure). FIG. 4B shows the SPE bed after 1.5 minutes, with a total of $1.4 \times 10^{-16}$ moles of BODIPY reagent loaded on the bed (assuming complete capture of the dye). No sample breakthrough was observed with BODIPY, due to its high affinity for the ODS material. In fact, visual observation indicated that after concentrating 1.0 n M BODIPY solution for two minutes only 5% of the physical volume of the SPE bed was utilized suggesting that the capacity of the 330 pL bed was about $2.8 \times 10^{-15}$ moles of analyte. A buffer wash step was used after loading to wash sample remaining within the channel 11 onto the bed (in chamber 4). The solutions in reservoirs 1 and 2 were then replaced with acetonitrile, and the dye was eluted with solvent moving in the same direction as the initial loading step (or by reversal of the potential gradient during the elution step, it could be directed back towards the original sample reservoir). Both procedures work well, but the latter was more convenient for our testing. FIG. 5 shows graphically the 3-step preconcentration experiment for a 1.0 nM BODIPY sample following bed equilibration. The 90-second loading step showed an increase in signal as the fluorescent sample passed by the detector positioned as shown in FIG. 1A. This was followed by a 60-second rinse step. Acetonitrile was then used to elute the BODIPY reagent off the bed in the opposite direction to which it was loaded, eliminating the need for detector repositioning. The BODIPY reagent eluted in a relatively narrow 3 second band following a 90 second preconcentration step exhibiting a many fold concentration increase compared to the original sample. The fluorescence of the BODIPY (1.0 nM) reagent was tested in both buffer and acetonitrile and did not show a significant difference in intensity for either of the solvents. The preconcentration factor (P.F.) can be estimated using equation (1):

$$P.F. = \frac{V_f}{V_i} = \frac{t_{pre} \cdot f_{buff}}{t_{elute} \cdot f_{elute}} \quad (1)$$

where Vi is the volume of buffer containing analyte and V f is the volume of acetonitrile containing analyte. The volume Vi is the product of the preconcentration time ($t_{pre}$, sec.) and the electroosmotic flow of the sample being concentrated ($f_{buff}$ L/sec.) while Vf is the product of width of the eluted analyte peak ($t_{elute}$, sec.) and the flow rate of the eluting solvent ($f_{elute}$, L/sec). For this case, the analyte was preconcentrated by a factor of at least 100 times. After sufficient concentration the BODIPY is easily observed visually on the SPE bed.

Different sample loading times were utilized to increase the amount of preconcentration. In the experiments, preconcentration times ranging from 120-532 seconds were studied yielding preconcentration factors of 80-500. Peak area (rsd 3-11%) plotted versus preconcentration time yielded a linear relationship (r2=0.9993) over the studied conditions.

Capillary Electrochromatography (CEC) On Chip

Figure 6:
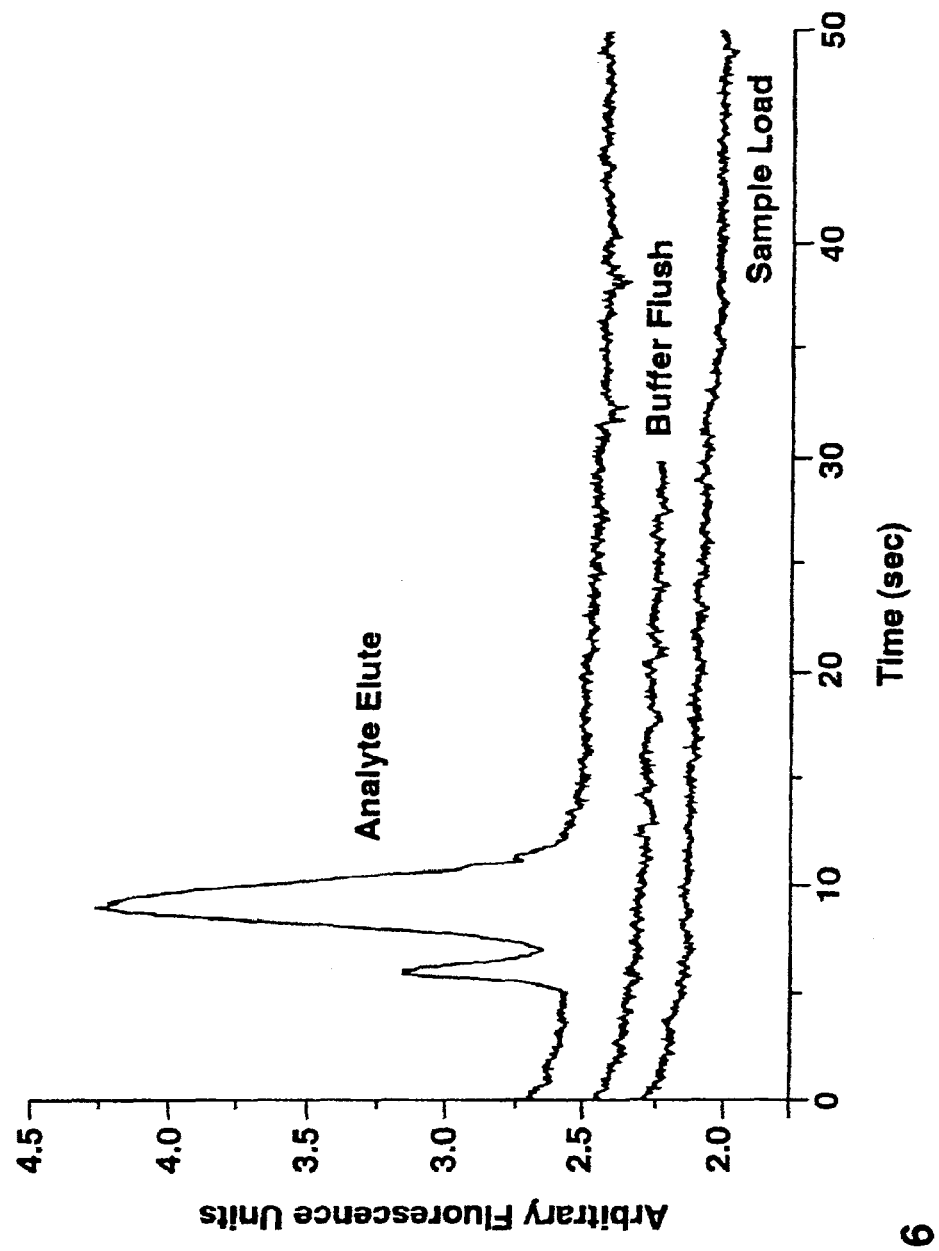
FIG. 6 shows an electrochromatogram of BODIPY and fluorescein, showing different steps of the separation including load, flush, and elution.
Figure 7A:
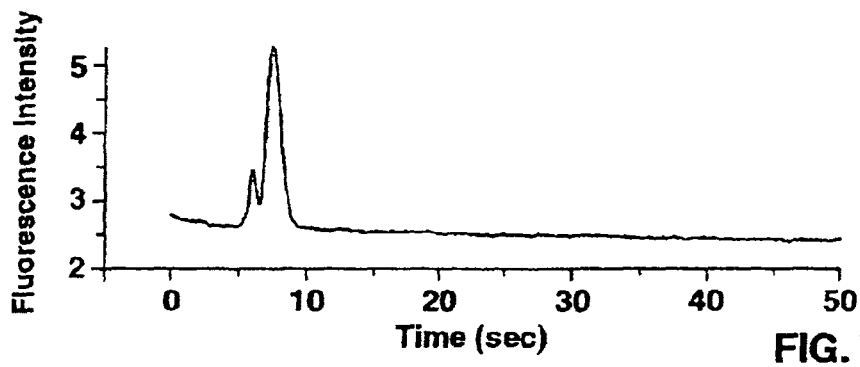
FIGS. 7A-7D show electrochromatograms of BODIPY and fluorescein with different concentrations of acetonitrile in the mobile phase, specifically at: (a) 30%; (b) 22%; (c) 15%; and (d) 10%.
Figure 7B:
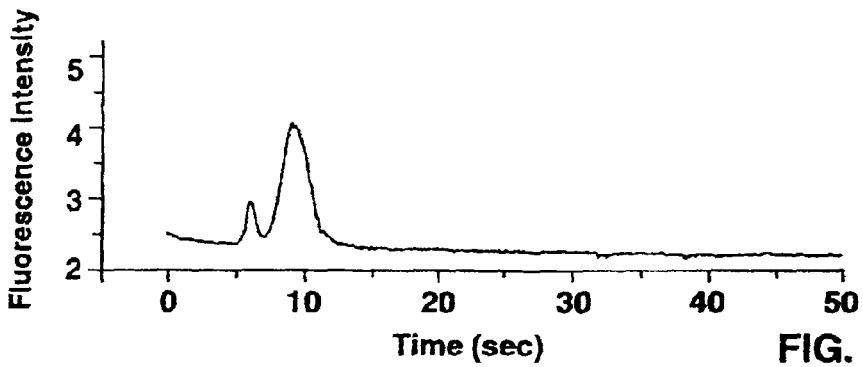
Figure 7C:
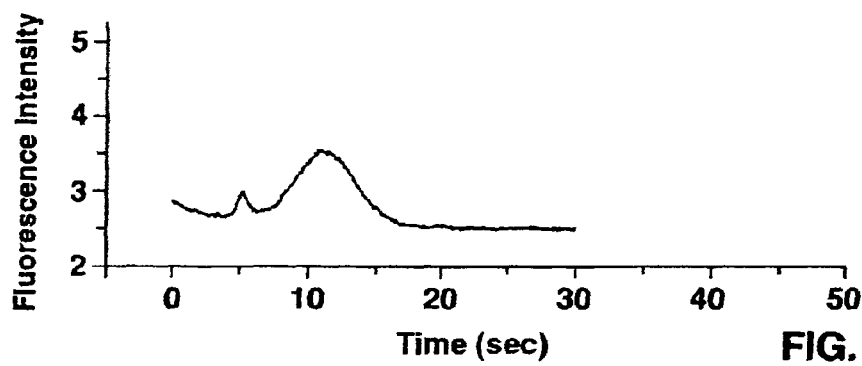
Figure 7D:
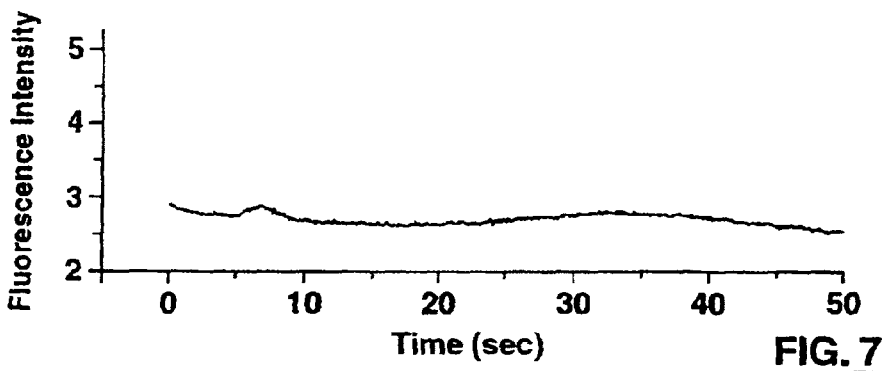

As explained earlier, another application facilitated by the present invention is on-chip capillary electrochromatography (CEC). Reversed phase mode CEC was performed on a chamber 4 packed with octadecyl silane beads 12 equilibrated with buffer. Due to the lack of an injector within the chip design, the samples were loaded onto the front of the chromatographic bed in 50 mM ammonium acetate buffer, pH 8.5 (see "Solutions and Reagents," above). Both compounds were totally retained under these conditions, as indicated by a lack of analyte signal in the loading and flush steps. The loading step functioned to both introduce the sample and preconcentrate the retained analytes at the front of the bed [Swartz, M. E.; Merion, M.; J. Chromatogr, 1993, 632, 209 213.] FIG. 6 shows the three steps involved in the CEC separation of BODIPY and fluorescein with a mobile phase composition of 30% acetonitrile/70% aqueous 50 mM ammonium acetate. Once the mixed mobile phase reaches the bed, both compounds begin to undergo chromatography and are eluted from the bed. The compounds are completely eluted and separated in less than 20 sec on less than 200 μm of chromatographic bed, yielding a plate height of 2 (N=100 plates or 500 000 plates/m) for the fluorescein peak. Under these conditions, the fluorescein is eluted prior to the BODIPY reagent. Peaks were identified by comparing retention times of the standards with those of the mixture. At pH 8.5 fluorescein possesses a net (−2) charge while BODIPY is neutral. In a normal CZE separation the electrophoretic mobility of fluorescein would oppose the EOF, causing the BODIPY to elute prior to fluorescein. In this case the elution order of the two components is reversed, indicating an interaction between the analytes and the stationary phase. The BODIPY being more hydrophobic has a higher affinity for the chromatographic material than does fluorescein causing the BODIPY to be retained more and eluted later.

Finally, FIGS. 7A-7D shows the CEC separation of BODIPY and fluorescein utilizing mobile phases with different concentrations of acetonitrile. It was observed that the increased acetonitrile concentration lowers the polarity of the mobile phase, decreasing the amount of time required for the BODIPY to elute. The elution time for fluorescein does not change, indicating little to no chromatographic retention except at low % acetonitrile. Decreasing the acetonitrile concentration provides baseline resolution, but leads to more extensive band broadening.

Our present results are comparable to that reported for open tubular CEC on a chip [Jacobson, S. C., Hergenroder, R., Koutny, L. B., Ramsey, J. M. Anal. Chem. 1994, 66, 2369 2373. Kutter, J. P.; Jacobson, S. C.; Matsubara, N.; Ramsey, J. M. Anal. Chem. 1998, 70, 3291 3297. He, B., Tait, N., Regnier, F. Anal. Chem. 1998, 70, 3790 3797.].

Immunoassay Using Bead Based Reagents

Immunoassay on beads, or immunosorbent assays involves placing either an antibody or antigen on the surface of the bead. As a solution containing an antigen passes over the beads, the antigen specifically binds the antibody. In this way the specificity of the antigen for the antibody is utilized to separate it from other species in solution. Later the solution conditions are changed so that the antibody or antigen is eluted from the beads and is detected as either complex or the free antibody. The development of immunosorbent assays on chip is attractive because of the small amounts of reagents that are consumed. In addition microchips offer very fast analysis times compared to conventional methods performed in micro titer plates or in syringes packed with immuno beads. Immunosorbent assays on chip also provide lower concentration detection limits than solution phase immunoassays on chip, making the development of bead based immunoassay on chip important.

Beads that have specific enzymes linked to them are packed into the chamber created by the two weirs. The use of beads is preferential because of the increased surface area of the beads as opposed surface area of the channel walls. The higher surface area leads to a greater capacity and more efficient trapping of the analyte. The weirs form a well defined chamber for the immunoassay beads to pack. The inventors have demonstrated bead based immunoassay on chip for the enzyme theophylline. In the experiment magnetic beads coated with protein A are packed within the chamber of the chip. Later the antibody (antitheophylline) is flowed across the bed in a 1 mM tricine buffer pH 8.0. When the antitheophylline flows through the packed bed the antibody binds to the protein A. The antitheophylline was passed over the bed for several minute to ensure that the bed is saturated with antibody. A buffer washing step was then utilized to remove the remaining unbound antibody from the chamber and channels. The bed was then saturated with fluorescently labelled theophylline (diluted from a kit) by flowing it through the bed where it binds to the antitheophylline. The point at which the bed was saturated was determined by monitoring fluorescence below the bed and determining the point where the breakthrough curve (FIG. 1) plateaus. Following breakthrough the theophylline solution is washed from the device using a buffer flush step. A chaotropic agent is then added to elute the theophylline from the bed as either free protein or theophylline/antibody complex. Chaotropic agents can be of various types, however in this example a mixture of 90% acetone/10% tricine buffer was used. Once the chaotropic agent reaches the packed bed the theophylline is eluted in a relatively narrow band (FIG. 2).

Although normally under these circumstances a competitive assay would be performed the direct assay demonstrates the ability of the chamber formed by the weirs to act as an immunoassay bed.

Enzyme Reactor Beds

There have been several methods developed for immobilizing enzymes onto solid supports like beads. Once immobilized the enzyme beads can be packed into beds to perform chemical reactions on solutions as they are flowed through them. Normally a solution containing a substrate is passed through the bed. When the substrate comes in contact with the enzyme the enzyme reacts with the substrate to yield a product. The product resulting from the reaction of the immobilized enzyme and substrate can be later used as a method of detection or in other synthetic processes. This example illustrates the use of the immobilized enzyme horse radish peroxidase (HRP) and xanthine oxidase (XO) on porous silica beads (5 μm diameter). These results show that enzymes, once immobilized onto beads, can be trapped/packed into the weir device, where they are still active and can be used as an enzyme reactor bed.

XOD and HRP were immobilized onto Nucleosil 1000 5 silica beads (Machrey Nagel, Germany) that had been silanized with 3-aminopropyltriethoxysilane, by crosslinking with gluteraldehyde (Sigma). The immobilization of enzymes on glass beads has been described previously and is known by practitioners of the art. All studies were performed using 50 mM boric acid adjusted with 1 M NaOH to pH 9. The immobilization of HRP and XOD was performed to demonstrate two principals. First was the ability to pack the enzyme immobilized beads within the weir device and then second was to demonstrate that the enzyme was still active and could be utilized to catalyze reactions once packed. To show each of these principals a chemiluminescent reaction was performed using the weir device.

The ability to pack immobilized enzymes allows different methods of detection to be used for certain analytes. For example the luminol chemiluminescence (CL) reaction can be used for very sensitive determinations when only small amounts of analyte are available or when labeling reactions are otherwise difficult to perform. CL reactions are unique in that they do not require a light source simplifying the detection scheme. The chemiluminescence reaction catalyzed by HRP is shown below.

Luminol+$H_2O_2$+HRP(Light(425 nm)+other products

Beads immobilized with HRP were packed into the weir device and a solution containing the reagents for the reaction passed through the bed. The immobilized HRP was found to catalyze the chemiluminescent reaction when a solution of $H_2O_2$ (100 (M) and luminol (10 mM) was flowed over a bed that had been packed with beads containing immobilized HRP. Light generated from the reaction was detected downstream from the enzyme bed.

However, it was noticed that with each successive trial the light generated from the CL reaction was lower than in the previous trial FIG. 1. This is probably caused by a decrease in the activity of the enzyme with each successive run. These results evidence the advantage of a method of removing the exhausted beads and replacing them with fresh ones, such as discussed for the replacement of ODS beads within the weir device.

ALTERNATIVE EMBODIMENTS

While a two weir embodiment of the design according to the present invention has been described above, other embodiments are also possible. For example, it is possible to implement a single weir design to form an on-chip reactor bead (i.e. not having a second weir 6 located upstream in the main channel 11). Specifically, by providing a downstream weir 7 formed across the main channel and providing pressure only in a downstream direction (i.e. from main reservoir 2 and side channel 3 to main reservoir 1), it has been observed that packing can be achieved against the downstream weir 7. However, it is noted that a single weir design may result in the formation of a ragged leading edge for the packed bed that reduces separation efficiency when used for SPE or CEC. Additionally, the high back pressure associated with a long bed of small beads limited the length of the pack to about 4-6 mm. A high pressure fitting for the microchip would allow high pressure pumping and allow somewhat greater lengths.

Other types of forces may also be used to create a packed bed using a single weir design. For example, it was also possible to achieve a limited degree of packing (to a length of a few millimeters) using electrokinetic forces, directed only in a downstream direction (i.e. from main reservoir 2 and packing material reservoir 3, to main reservoir 1).

In addition to varying the number of weirs, it is also possible to provide more than one inlet or outlet to a chamber, as shown in alternative embodiments of the present invention in FIGS. 8A-8C.

In FIG. 8A, a chamber 4 is formed between two weirs 6, 7. Two side channels 5 *a*, 5 *b* are provided to serve as an inlet or outlet to the chamber 4. As shown in FIG. 6, the side channels 5 *a*, 5 *b* may be offset relative to each other to better facilitate packing of the chamber. A second side channel is added to allow the beads to be flushed out to waste at the other end of the trapping zone, or to allow the flushing agent to be delivered from an alternate reservoir. The latter design can prevent used beads from contaminating the fresh bead stream, and/or prevent sample and sample waste solutions from being directed into the trapping zone during flushing.

As shown in FIG. 8B the side channel in this design may have one or more optional branches 5 *c*, to allow the side channel 5 *b* to be flushed of beads, or to allow beads being flushed out of the trapping zone to be directed, for example, into a waste reservoir instead of into the packing material reservoir 3 (not shown).

Another embodiment is shown in FIG. 8C, in which a side channel weir 16 is provided near the entrance of a third side channel 5 *d* to the chamber 4, to allow fluid flow without passage of beads. This "weired" side channel 5 *d* may be used, for example, to release pressure build up in the chamber 4 during loading of the beads, particularly when the length of the chamber 4 (as measured between the weirs 6, 7) is greater than 4-6 mm.

In all three embodiments shown in FIGS. 8A-8C, the side channel entrance into the chamber 4 may be modified to include a hook or similar shape, as described earlier, in order to prevent direct "line of sight" flow from a side channel into the chamber 4, or vice versa. As explained earlier, this entrance modification serves to spray the beads into the trapping zone in order to assist packing, and to reduce the tendency of the beads to exit from the chamber 4 during later use.

Loading of beads with more than one side channel, as shown in FIGS. 8A-8C, is performed in a manner similar to that for a single side channel, two weir design, (as described above) except that a potential must also be applied to the additional side channels to prevent flow into those side channels when using electrokinetic loading. During removal of the beads a voltage may be applied to a second side channel (e.g. side channel 5 *b* in FIG. 8A) to drive beads out of the trapping zone or chamber 4, applying voltage potentials such as those used with the single side channel design but adjusted for the potential drop in the additional side channel. As will be appreciated, the direction of flow during the flushing step can be controlled by the polarity of the applied voltage.

When using pressure driven flow to load beads, a back pressure must be applied to the additional side channels during loading, or else the reservoirs attached to the additional side channels may be temporarily sealed. When flushing the beads from the chamber 4, a pressure may be applied to the bead supply channel 5*a* to flush beads out of one or more additional side channels.

When performing SPE or CEC using a multiple side channel design and electrokinetic forces, a voltage may be applied to the additional side channels to prevent leakage of sample or beads out of the trapping zone and into the side channels, substantially in the same manner as described for a single side channel in the trapping zone. When using pressure driven pumping, the side channels may a have enough positive pressure applied to eliminate flow into the side channel, or else the reservoirs attached to the respective side channels can be temporarily sealed.

Immobilizing the Packed ODS Beads with Polymer

After packing the chromatographic bed with beads using electrokinetic, magnetic or pressure packing techniques, a reasonable portion of the bead introduction channel was then packed with the beads using one of these packing techniques. Excess beads in the reservoir were then removed. Then about 40 ml of a monomer mixture was pipeted into the bead reservoir and delivered by pressure or electrokinetic flow along the bead introduction channel, towards the beads. During this step, a change in refractive index in a region within the bead introduction channel was used to monitor the position of the monomer solution, and flow was stopped well before the monomer reached the packed bead bed.

A typical monomer solution may be prepared as follows: to a vial that contained 800 ml of a ternary solvent mixture that contained 10 wt % $H_2O$, 40 wt % 1,4-butanediol and 50 wt % 1-propanol, 200 ml of a mixture of 2,2'-azobisisobutyronitrile (AIBN, 2 wt %) and ethylene dimethacryllate (EDMA) was added. (C. Peters et al, *Anal. Chem.* 1997, 69, 3646-3649.) This monomer solution was then purged with $N_2$ for 15 min to remove dissolved oxygen. Other polymerizable solution of monomer may be used.

The device was then kept in an oven at 60° C. for 24-48 hr. The device was taken out from the oven and cooled down to room temperature, with all reservoirs covered to prevent evaporation. Alternatively, photo-initiated polymerization with AIBN or other initiator may be used to polymerize the monomer solution, without a need for extended heating of the device. Following polymerization the device was rinsed with acetonitrile then with buffer. Mobile phase compositions of up to 100% acetonitrile could be used in such devices without destabilizing the bead bed.

Dimension Guidelines

While the theoretical limits of various dimensions of a microfluidic device designed according to the present invention are not known, the inventors have adopted some general guidelines for practical purposes, which are discussed below.

It is thought that the length of the trapping zone may range anywhere from about 10 μm up to about 200 cm (using a coiled or serpentine path if necessary to allow for incorporation of such a length within the confines of a single device wafer). The trapping zone length required will be dependent upon the application and will also be limited by the forces which may be applied to achieve packing and unpacking. For example, on-chip CEC would require relatively long trapping zones, with a preferred upper limit of about 5 cm.

As to the depth of the trapping zone, sample and waste channels, a practical range is estimated to be about 400 μm to 0.25 μm. More preferably, the upper limit should be about 100 μm and the lower limit should be about 10% larger than the particle depth at a minimum.

Also, in order to reduce the likelihood of clogging, the bead delivery and bead waste channels (side channels 5, 5 *a*-5 *d*) preferably should be at least about 3 times deeper and three times wider than the bead diameter.

The maximum dimensions of the side channels 5, 5 *a*-5 *d* are also dependant upon the relative flow resistances required (i.e. the flow resistance of the side channel versus the main channel and the weirs, so as to minimize side channel backflow during use). Generally speaking, the flow resistance of the side channels should be higher than the flow resistance of weirs to minimize the backflow problem.

The accompanying tables provide information on the calculated effect of channel and weir dimensions on the volumetric flow rates out of the trapping zone, as a function of flow channel depth, weir depth and side channel length using pressure driven flow.

In the tables below, what is called channel W is element 1 in FIG. 1A; what is called channel C is called element 5 in FIG. 1A; and what is called channel C' is element 3 in FIG. 1A

| Correlation to FIG. 1A | | Width | Length |
|---|---|---|---|
| | 20 μm Deep | | |
| Element 1 | Channel W | 600 | 6,500 |
| | Weir | 280 | variable |
| Element 5 | Channel C | 50 | variable |
| Element 3 | Channel C' | 600 | 3,500 |
| | 10 μm Deep | | |
| Element 1 | Channel W | 580 | 6,500 |
| | Weir | 280 | variable |

The volumetric flow rates were estimated using the Navier Stokes equation for a rectangular channel cross section and Perry's tabulated values of the effect of channel shape. The flow resistance of a channel with half width and a half depth b is given by equation 2:

$$\Delta P/U = hL/abN \qquad (2)$$

where $\Delta P$ is the pressure drop along a channel segment of length L, U is the average linear flow velocity, h is the viscosity, and N is a form factor dependent upon the cross sectional ratio b/a (b<a). The factor N may be estimated from solutions to the Navier Stokes equation for pressure driven, parabolic flow, and was tabulated by Perry in Chemical Engineer's Handbook, (3rd edition, 1950) pp 387. The goal in device design is to make the resistance of the side channel, C in the Tables, higher than the resistance of the weir and the following flow channel W, so that flow across the weir is favoured. When flow elements are in series the fluid resistance given by the right hand side of equation 1 for each segment can be added in the manner that the resistance of series electrical impedances can be added. When fluid elements are in parallel the inverse of their fluid resistance can be added to obtain the inverse of the total impedance, as is done for parallel electrical resistances. The volumetric flow rate, Q, through a channel or a combination of channels is then given by equation 3.

$$Q = ab\Delta P/Rf \quad (3)$$

Where Rf is the resistance to fluid flow defined by the right hand side of equation 1, combined together for all channel segments as discussed above. The ratio, r, of volumetric flow rate across the weir, $Q_w$ versus into the side channel, $Q_C$, $r=Q_w/Q_C$, should be large to ensure the percent of solution flowing across the weir, $\% Q_w = 1/(1+r)$, is high. This can be accomplished by using a long narrow side channel compared to a wide main channel, by increasing the depth of the weir relative to the depth of the other channels, by decreasing the depth of the side channel relative to the main channel, etc, as indicated by several calculations presented in the Tables.

TABLE

Volumetric Flow Ratios for 10 and 20 μm Deep Designs

| Channel depth | Channel C Length | Weir Depth | Weir Length | Volumetric ratio r | % Qw |
|---|---|---|---|---|---|
| 20 μm | 15,000 | 3 | 20 | 12.58 | 92.6 |
|  | 25,000 |  |  | 20.85 | 95.4 |
|  | 15,000 |  | 10 | 18.75 | 94.9 |
| 20 μm | 15,000 | 1 | 20 | 0.687 | 41.1 |
|  | 25,000 |  |  | 1.16 | 53.6 |
|  | 15,000 |  | 10 | 1.37 | 57.8 |
| 10 μm | 15,000 | 3 | 40 | 38.9 | 97.5 |
|  | 25,000 |  |  | 63.7 | 98.5 |
|  | 15,000 |  | 30 | 41.7 | 97.7 |
| 10 μm | 15,000 | 1 | 40 | 4.14 | 80.5 |
|  | 25,000 |  |  | 6.87 | 87.3 |
|  | 15,000 |  | 30 | 5.83 | 84.3 |

TABLE

Fixed Device Dimensions for Calculations with a Given Etch Depth

|  | Width | Length |
|---|---|---|
| 20 μm Deep |  |  |
| Channel W | 600 | 6,500 |
| Weir | 280 | variable |
| Channel C | 50 | Variable |
| Channel C' | 600 | 3,500 |
| 10 μm Deep |  |  |
| Channel W | 580 | 6,500 |
| Weir | 280 | variable |
| Channel C | 30 | Variable |
| Channel C' | 580 | 3,500 |

Integrated Analytical Procedures

It will be appreciated that the various features of the present invention as described above may be utilized in a more complex microfluidic design.

Figure 9:
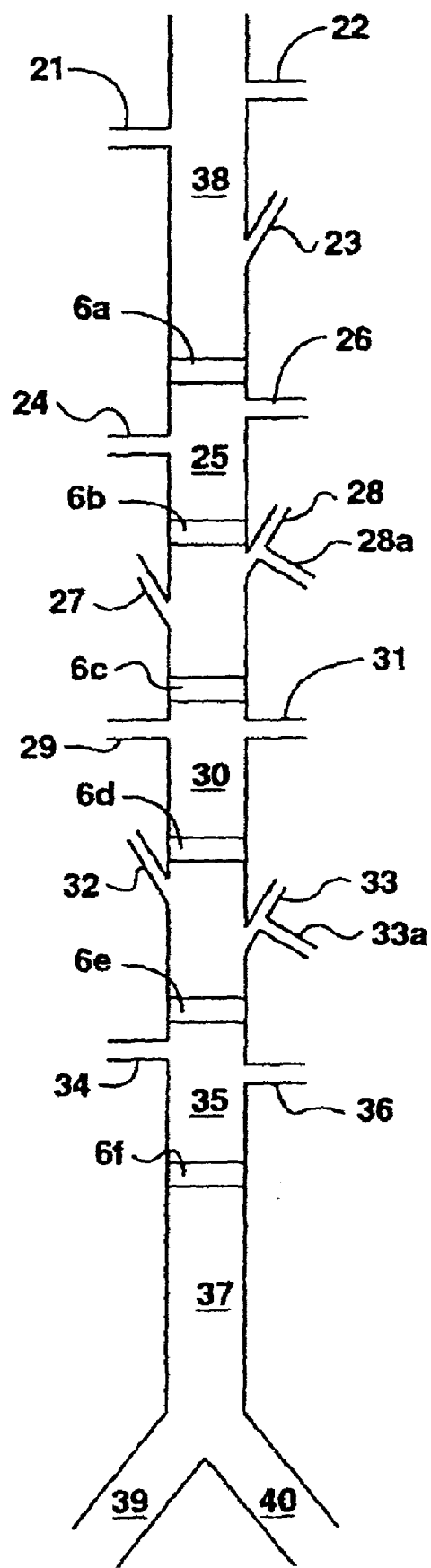
FIG. 9 shows a top plan view of a microfluidic device according to the present invention having multiple packed chambers.

FIG. 9 shows a multiple weir and multiple side channel design, generally referred to by reference numeral 20, in which several trapping zones are integrated, each serving a different function.

As an illustrative example, in a first trapping zone 25, formed between weirs 6 a and 6 b, beads loaded with an antibody to a specific protein are introduced via side channel 25 (and exit via side channel 26). A cell lysate or serum sample or other protein source is directed from a sample reservoir (not shown) and loaded into the chip via sample inlet 21 and entrance channel 38 (the sample is removed at sample outlet 22 and an eluent inlet 23 is also provided at the entrance channel. The sample is then passed into the antibody bead bed in trapping zone 25 to isolate a specific protein, while the effluent is directed towards waste outlet 27.

A chaotropic elution agent, such as an acetonitrile, water mix, is then introduced (eluent inlet 23) to elute the protein from the column and deliver it to the next trapping zone 30 (formed between weirs 6 c and 6 d) where it is digested by a protease enzyme immobilized on beads loaded into the zone 30 (via side channels 29, 31). The effluent at this stage would be directed towards waste outlet 32. After sufficient reaction time, a buffer is delivered (elution inlet 28, running buffer 28 a, waste from bed 25) to flush the protein digest from the bed and into the next trapping zone 35 (formed between weirs 6 e and 6f) with effluent delivered to waste outlet 39.

The third trapping zone 35 contains a solid phase extraction material (packed and unpacked via side channels 34, 35), allowing concentration of the digest peptides onto the bed in zone 35. An elution solvent, such as a methanol/aqueous mixture or acetonitrile/aqueous mixture is then introduced (elution inlet 33, running buffer 33 a) to deliver (exit channel 37, waste 39, or collection 40) a concentrated protein digest to another location on the chip for final analysis.

Packed Bed Chip to Electrospray Mass Spectrometry Interface

Figure 10:
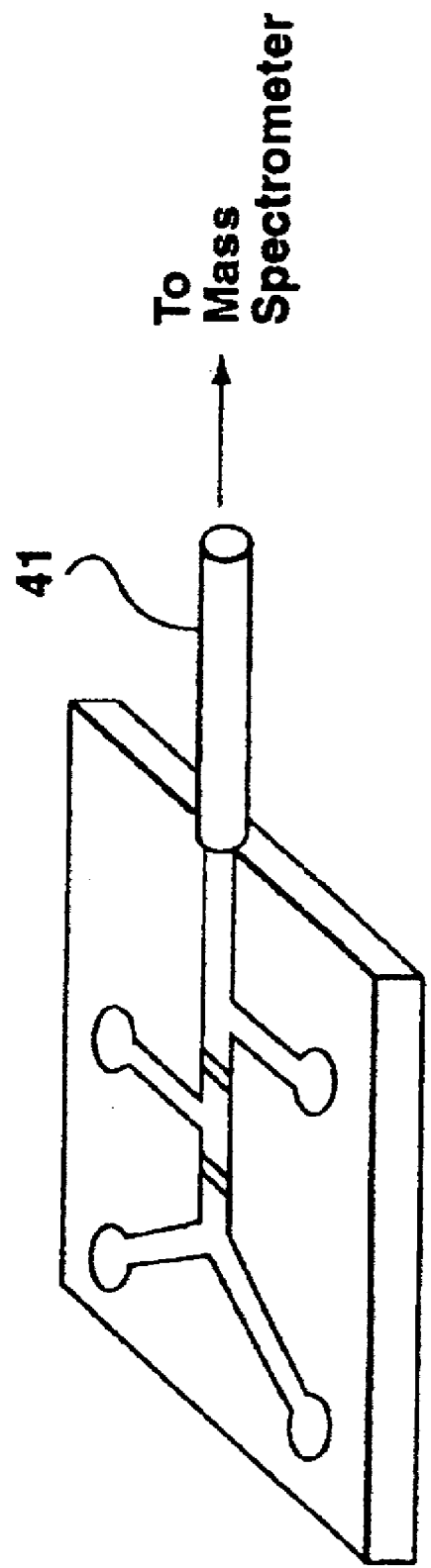
FIG. 10 shows a schematic view of a microfluidic device according to the present invention being used in conjunction with a mass spectrometer.
Figure 11:
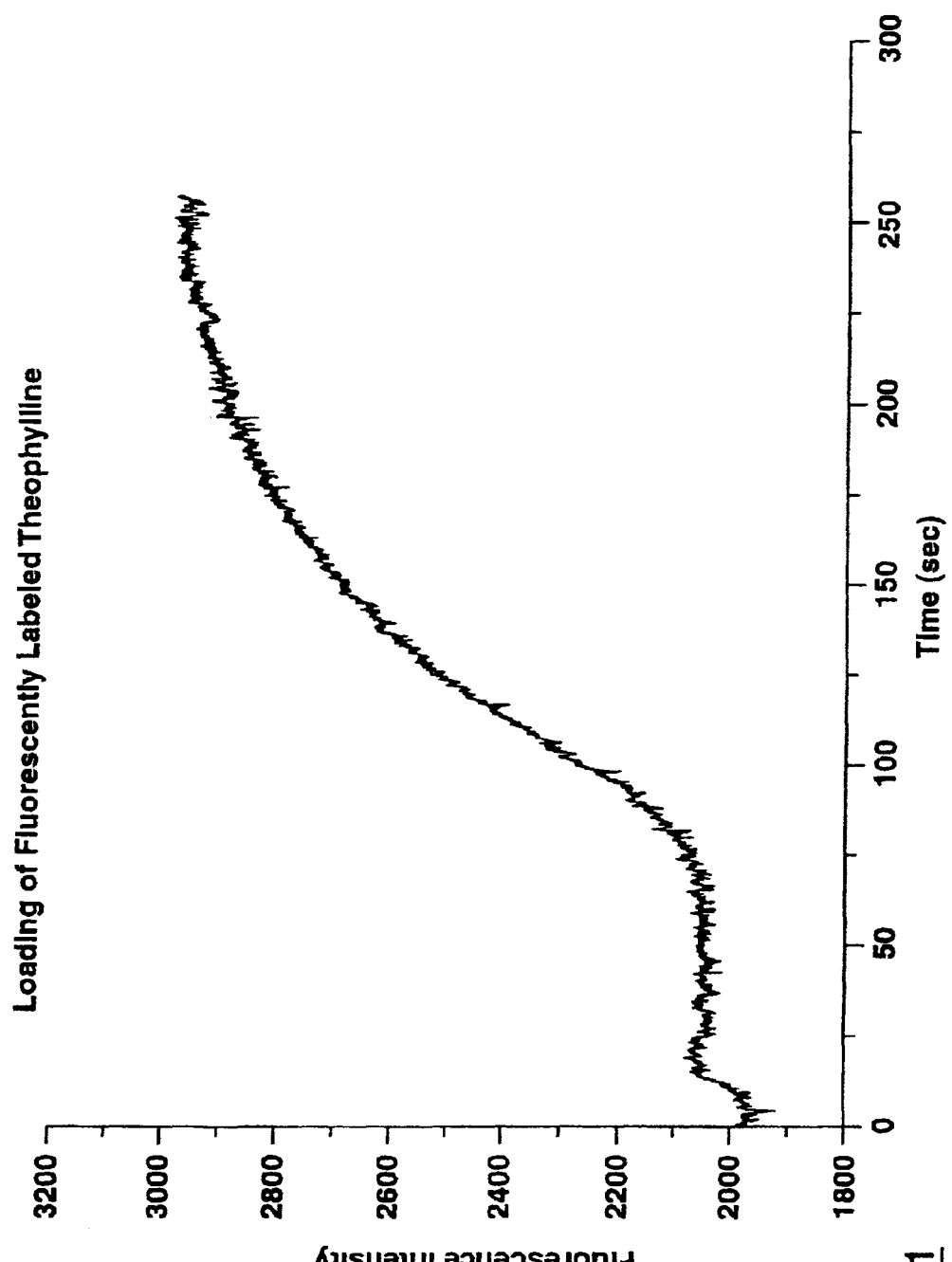
FIG. 11 shows a graph plotting the fluorescence intensity of theophylline against time, as it saturates a packed bed.
Figure 12:
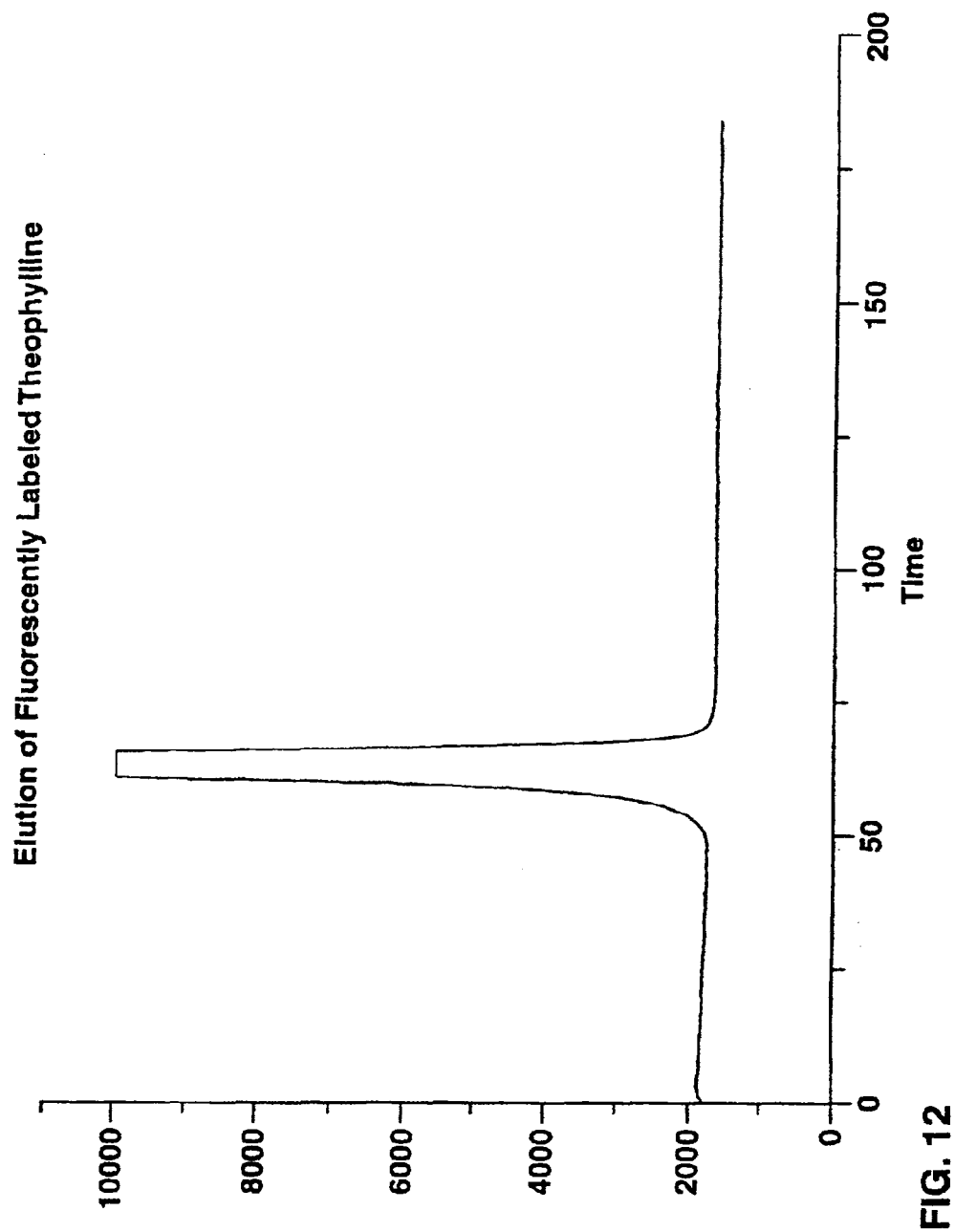
FIG. 12 shows theophylline being eluted from packed bed in a relatively narrow band.
Figure 13:
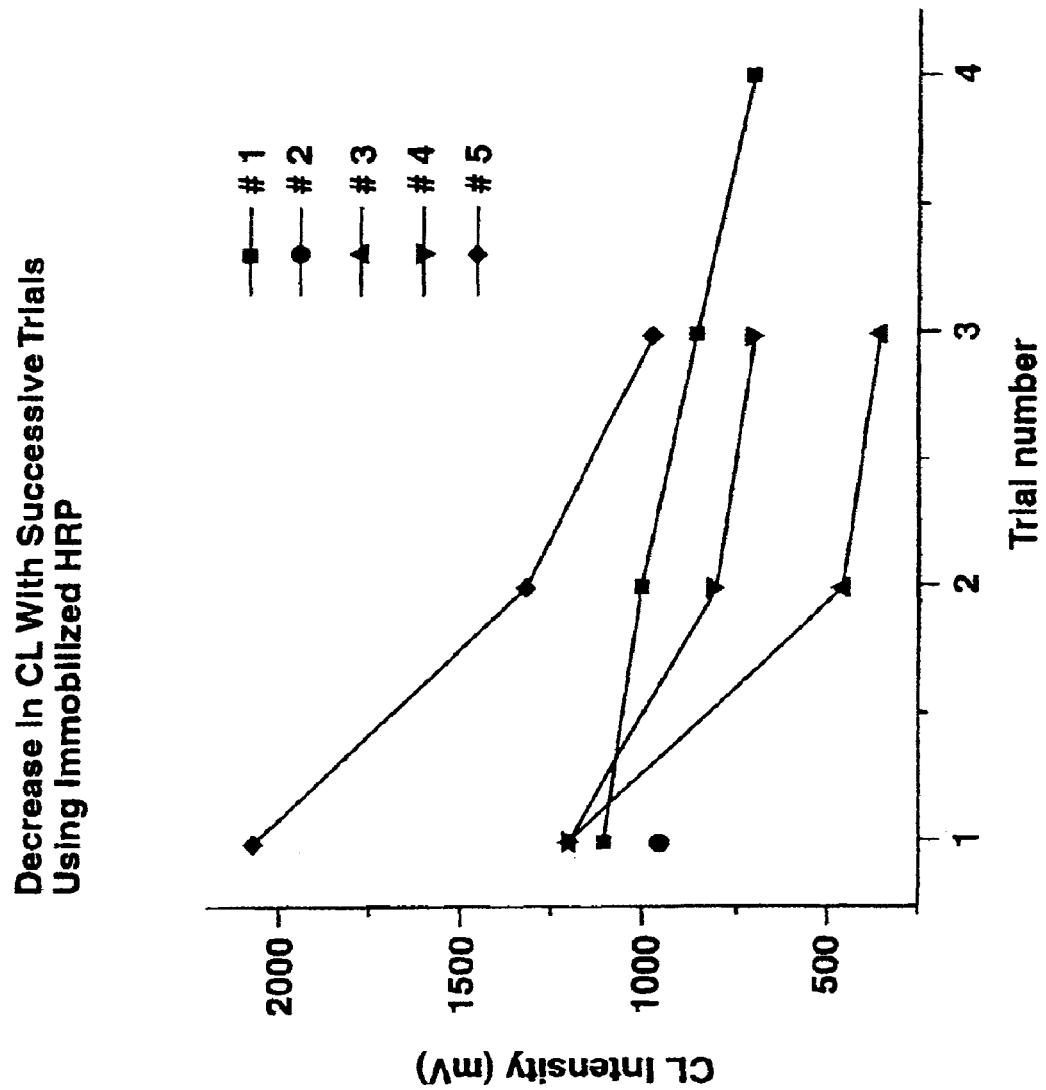
FIG. 13 shows each successive trial resulting in lower light generated from the CL reaction.

Packed bed flow channels according to the present invention may be interfaced to a mass spectrometer via an electrospray coupler 41, as illustrated in FIG. 10. The packed bed 4 may perform an enzyme digestion of a protein, affinity purification and pre concentration of a specific chemical or protein, solid phase extraction concentration enhancement, or capillary electrochromatographic separation, or any combination of these and other steps, prior to electrospray introduction in to a mass spectrometer. The chip to electrospray interface may be made using any method that provides a less than 100 mL dead volume, preferably less than 1 mL and most preferably less than 100 pL dead volume at the coupling region. A method such as that described by Wang et al., or Karger can be used to create the interface [Rings, N. H.; Wang, C.; Skinner, C. D.; Colyer, C. L.; Thibeault, P.; Harrison, D. J. Anal. Chem. 71 (1999) 3292 3296. Zhang, B.; Liu, H.; Karger, B. L.; Foret, F. Anal. Chem. 71 (1999) 3258 3264].

While the present invention has been described by reference to various preferred embodiments, it will be understood that obvious changes may be made and equivalents substituted without departing from the true spirit and scope of the invention which is set out in the following claims.

We claim:

1. A microfluidic analysis system, comprising:
   a) a substantially planar substrate having an upper surface;
   b) at least one main channel formed into said upper surface, said main channel having first and second ends and a defined direction of flow in use;
   c) a cover plate arranged over said planar substrate, said cover plate closing off said channel from above;
   d) a packing material having constituent particles that are non-polar, and
   e) a first weir formed across said main channel and between said first and second ends of said channel, said first weir providing at least one flow gap to allow, in use, at least some fluid to flow past said first weir while trapping said packing material the material comprising constituent particles that are generally larger than said flow gap.

2. The microfluidic analysis system claimed in claim 1, further comprising at least one side channel formed into said planar substrate, said side channel being connected at a first end to said main channel at a location upstream from said first weir, and at a second end to a reservoir, said side channel providing a higher flow resistance than said main channel.

3. The microfluidic analysis system claimed in claim 2, further comprising a second weir located upstream from said connected first end of said side channel, said first and second weirs forming a chamber therebetween, said second weir providing at least one flow gap to allow, in use, at least some fluid to flow past said second weir while trapping said packing material within said chamber.

4. The microfluidic analysis system claimed in claim 3, wherein, each side channel connection to said main channel is provided with a hook structure whereby, in use, packing material is sprayed into said chamber to facilitate even packing.

5. The microfluidic analysis system claimed in claim 4, wherein, said hook structure at least partially obstructs direct line-of-sight entry of packing material from said side channel into said chamber and forms a chamber mouth to one side of said hook structure.

6. The microfluidic analysis system claimed in claim 1 or 3, wherein, said flow gaps comprise a generally uniform gap between said cover plate and the top of said weirs.

7. The microfluidic analysis system claimed in claim 1 or 3, wherein, said flow gaps comprise a plurality of substantially vertical gaps in said weirs.

8. The microfluidic analysis system of claim 1, wherein, said system is formed entirely on a single microfluidic chip.

9. A method for analyzing a sample comprising the steps of:
   providing the microfluidic analysis system of claim 1, and,
   flowing said packing material into said main channel and trapping said packing material with said first weir to form a packed bed of packing material.

10. The method of claim 9, further comprising flowing a sample through said packed bed.

* * * * *